United States Patent [19]

Binder et al.

[11] Patent Number: 5,770,578
[45] Date of Patent: Jun. 23, 1998

[54] USE OF TRITERPENSAPONINS, SUCH AS NOTOGINSENOSIDE R1 (NR1) AND/OR ASTRAGALOSIDE (ASIV) FOR PREPARING MEDICAMENTS

[75] Inventors: Bernd Binder; Weijian Zhang; Johann Wojta, all of Vienna, Austria

[73] Assignee: Bergi GmbH, Vienna, Austria

[21] Appl. No.: 553,611

[22] PCT Filed: Mar. 16, 1995

[86] PCT No.: PCT/AT95/00049

§ 371 Date: Jan. 4, 1996

§ 102(e) Date: Jan. 4, 1996

[87] PCT Pub. No.: WO95/24905

PCT Pub. Date: Sep. 21, 1995

[30] Foreign Application Priority Data

Mar. 16, 1994 [AT] Austria .................................. 561/94

[51] Int. Cl.⁶ .................................................. A61K 31/705
[52] U.S. Cl. ........................... 514/26; 514/822; 514/885; 536/5
[58] Field of Search ............................ 514/26, 822, 885; 536/5, 6, 6.1, 6.3

[56] References Cited

U.S. PATENT DOCUMENTS 4,708,949  11/1987  Liu ............................................ 514/26
4,795,742   1/1989  Liu ............................................ 514/26

OTHER PUBLICATIONS

Pan et al., *Chin. J. Pharmacol. Toxicol.*, vol. 7(2): 141–144, (1993). Abstract only.
Zhao et al., *Immunopharmacology*, vol. 20(3): 225–234, (1990). Abstract only.
You–Tang et al., *Acta Pharmacol. Sin.*, vol. 7(5): 439–442, (1986). Abstract only.
Matsuda et al., *Chem. Pharm. Bull.*, vol. 34(3): 1153–1157, (1986). Abstract only.
Kubo et al. *Yakugaku Zasshi*, vol. 104(7), pp. 757–762, (1984).
Planta Medica, vol. 55, No. 1, pp. 18–21, Feb. 1989.
Chem. Pharm. Bull., vol. 34, No. 5, pp. 2100–2104, May 1986.
Chem. Pharm. Bull., vol. 34, No. 3, pp. 1153–1157, Mar. 1986.
Chem. Pharm. Bull., vol. 39, No. 5, pp. 1185–1188, 1991.
Annals of Hematology, vol. 70, Supplement 1, p. A92, 1995.
Fibrinolysis, vol. 8, Supplement 1, p. 119, 1994.
Fibrinolysis, vol. 8, Supplement 1, p. 150, 1994.
Chemical Abstracts, 104:183310j 1986.
Chemical Abstracts, 119:85683y 1993.
Patent Abstracts of Japan 55–127317, 1980.
Patent Abstracts of Japan 63–198609, 1988.

*Primary Examiner*—James O. Wilson
*Assistant Examiner*—Howard C. Lee
*Attorney, Agent, or Firm*—Herbert Dubno; Jonathan Myers

[57] ABSTRACT

The use of triterpensaponins, like notoginsenoside R1 (NR1) and/or astragaloside (ASIV) for the production of medicaments for stimulating the fibrinolytic activity and blocking the endotoxin effect, especially for the treatment of patients and animals which suffer from endotoxin shock or to limit the endotoxin shock. Corresponding medicaments are also suitable prophylactive and therapeutic treatment of patients of coronary heart disease, peripheral arterial disease for patients who suffer from angina pectoris and for the prevention of such diseases in healthy persons.

5 Claims, 19 Drawing Sheets

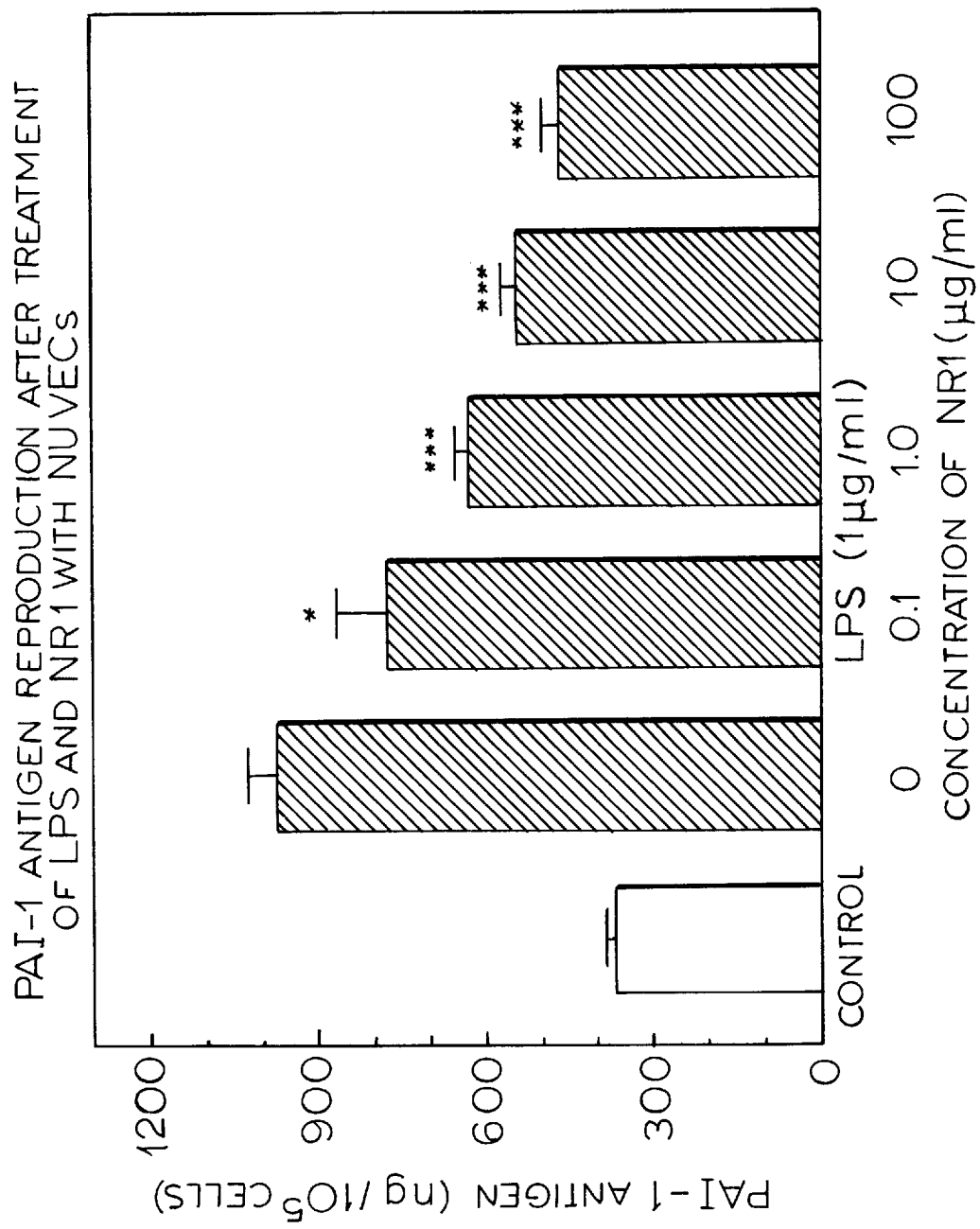

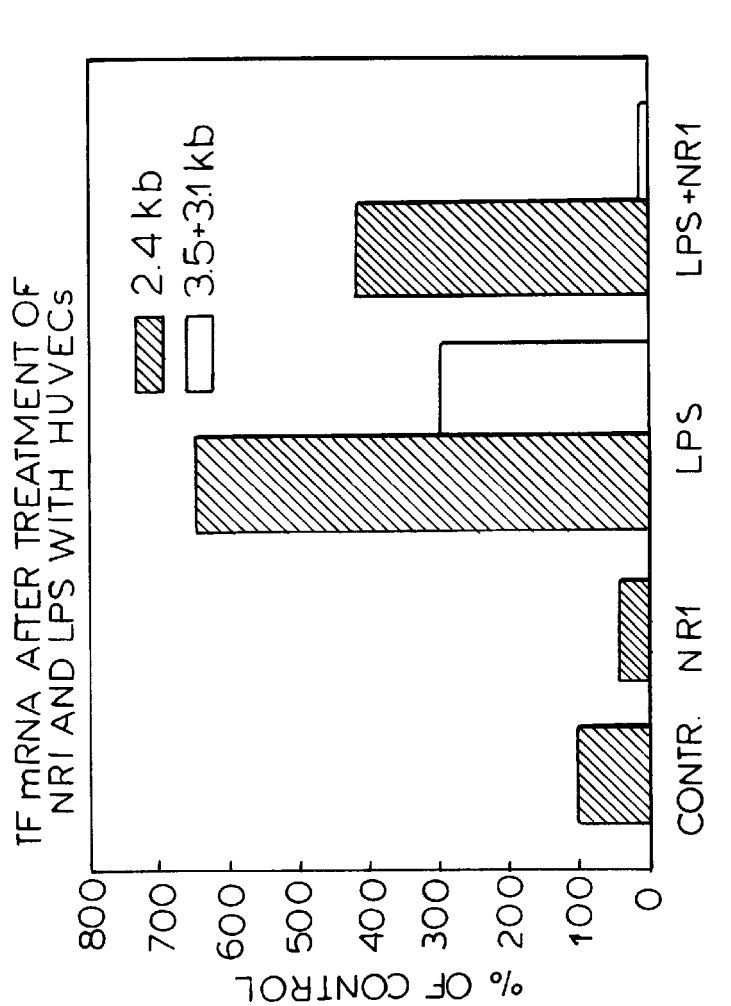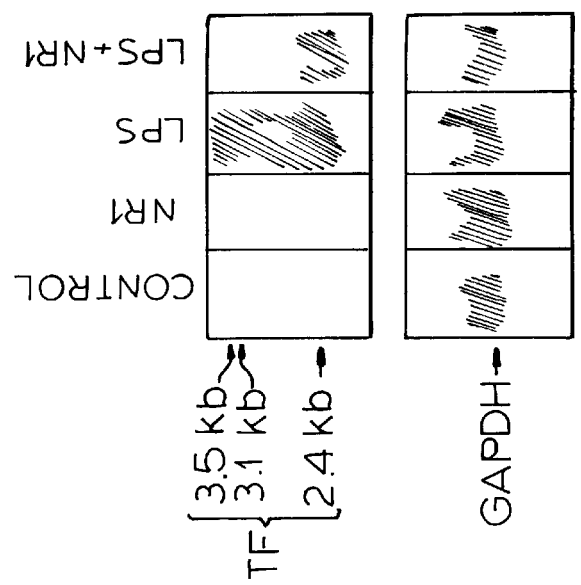
FIG.11

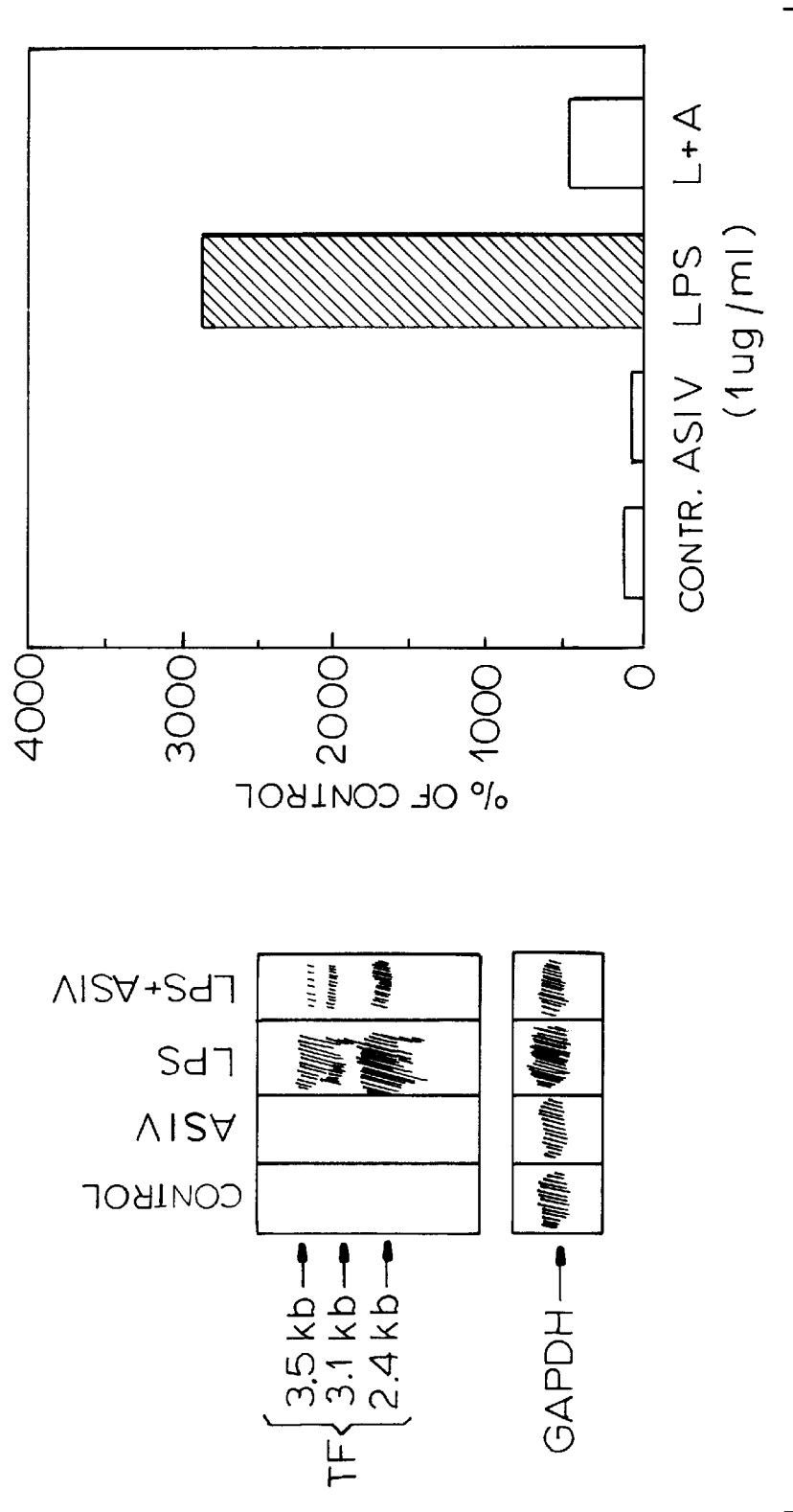

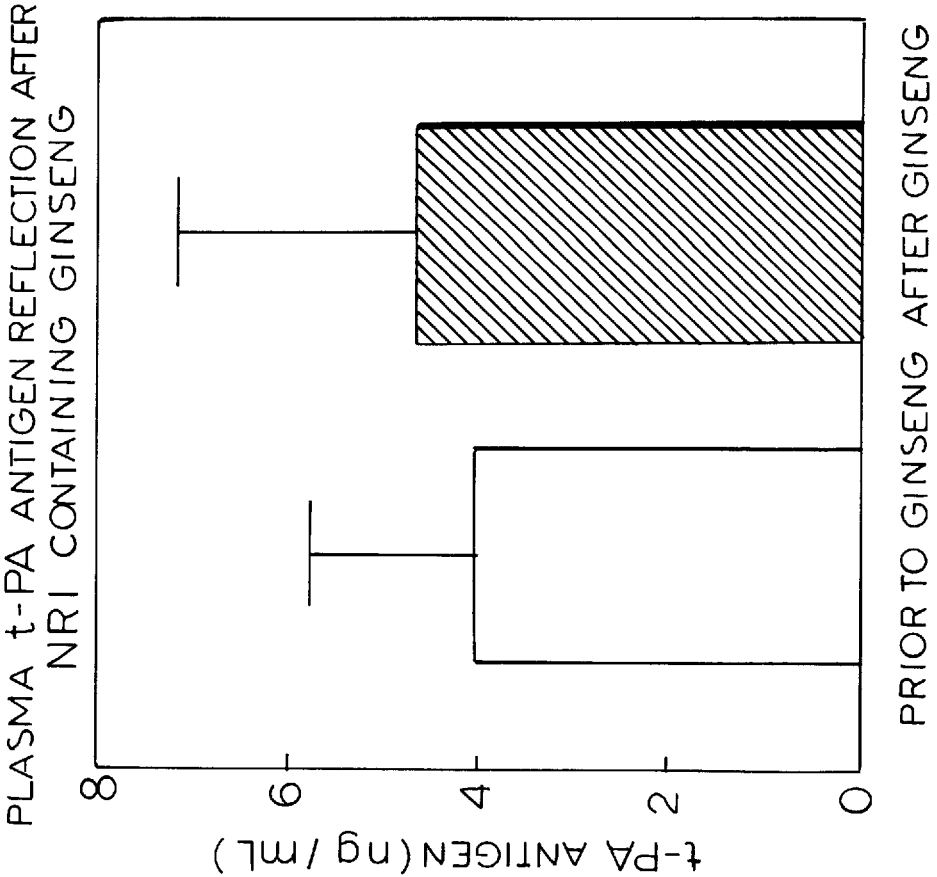

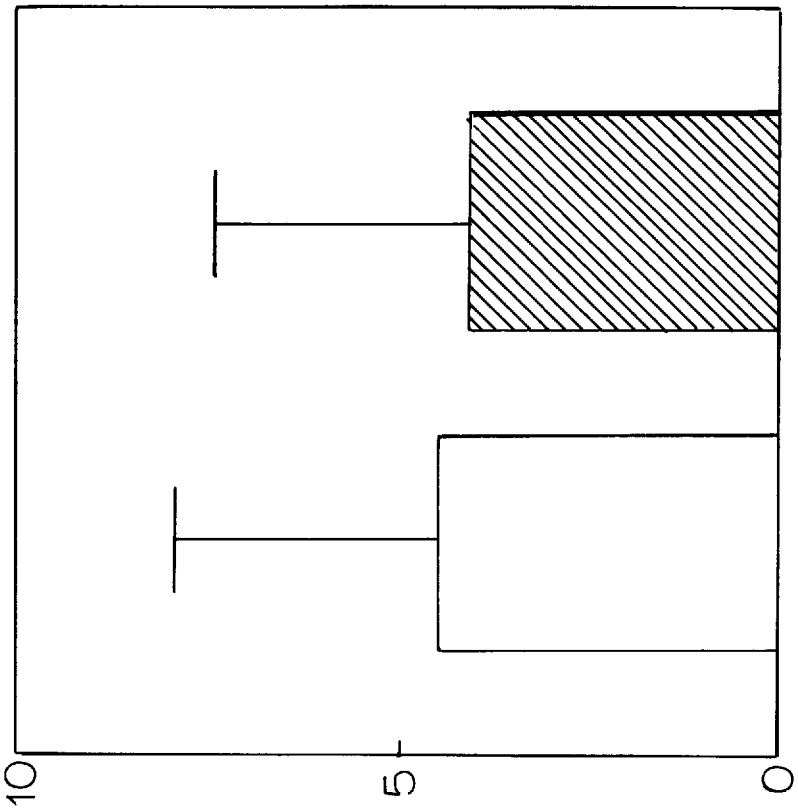

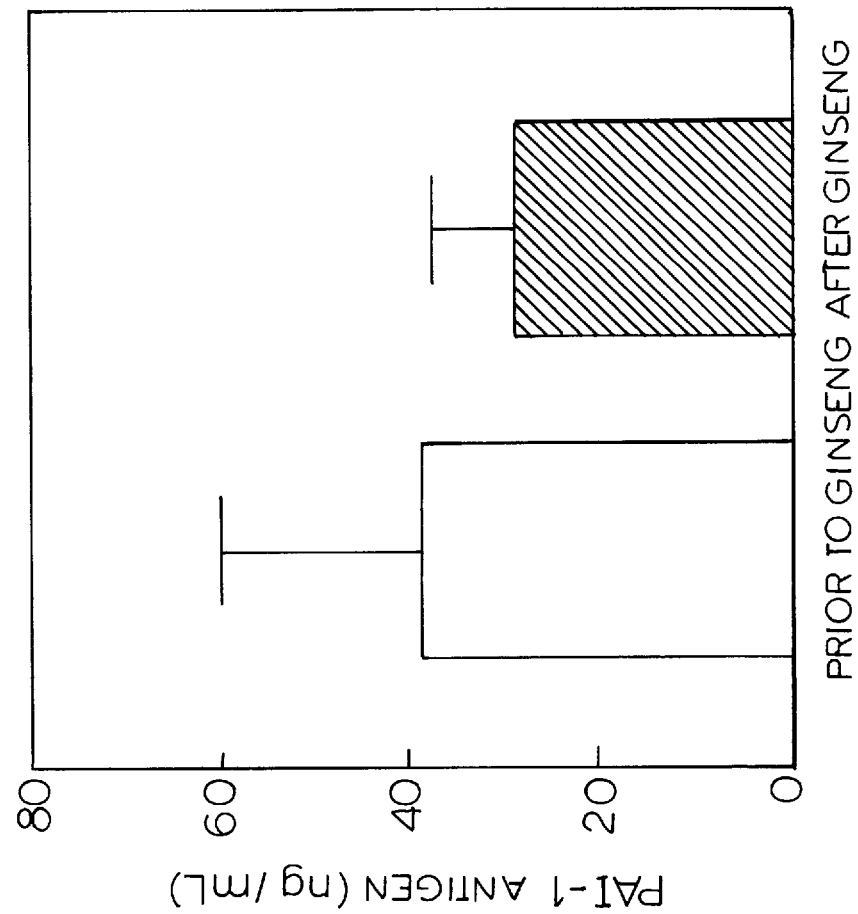

5,770,578

USE OF TRITERPENSAPONINS, SUCH AS NOTOGINSENOSIDE R1 (NR1) AND/OR ASTRAGALOSIDE (ASIV) FOR PREPARING MEDICAMENTS

SPECIFICATION

BACKGROUND OF THE INVENTION

The fibrinolytic system serves as a basic defense mechanism to control the deposition of fibrin both in the vascular as well as in the extra vascular systems. Proper functioning of the fibrinolytic system is necessary on the one hand to limit haemorrhagia and on the other hand thrombotic phenomena, but also to limit the formation of interstitial fibrin deposits and consequent scarring. It has been recognized that the tissue plasminogen activator (t-PA) plays an important role in the initiation of the (extrinsic) fibrinolytic cascade by the transformation of the zymogen plasminogen into the active plasmin that degrades fibrin. It has also been found that the fibrinolytic capacity of plasma is strongly dependent on the concentration of circulating t-PA. The t-PA in the plasma probably stems primarily from the vascular wall where it is localized in the endothelial cell. In addition, urokinase plasminogen activator (u-PA) plays a role in the overall fibrinolysis. It has been thought that this plasminogen activator—also at least partly—derives from the vascular wall. The main inhibitor of fibrinolysis, plasminogen activator inhibitor (PAI-1) is also synthesized by endothelial cells and data exists which shows that the relative proportion between PAs and PAI-1 is important for the fibrinolytic capacity and in turn for prevention of thrombotic events like, for example, myocardial infarction. The pharmacological regulation of t-PA, u-PA and PAI-1 synthesis is therefore useful to increase insufficient endogenous fibrinolysis.

Since both t-PA and also PAI-1 are produced by endothelial cells, the regulation of their synthesis and secretion at the level of the endothelial cell provides a rapid and direct way of influencing the fibrinolytic potential of the blood. Studies recently carried out have indicated that the production of plasminogen activators and inhibitors in various cell types is regulated by a series of factors: The synthesis of t-PA in endothelial cells is increased by a number of stimuli such as thrombin, histamine, butyrate, retinoic acid and tumor promoters as, for example, phorbol-12-myristate-13-acetate (PMA). Factors which regulate the PAI-I expression in endothelial cells include lipopolysaccharides, thrombotim, interleukin-1(IL-1), tumor necrosis factor $\alpha$, (TNF $\alpha$), transforming growth factor $\beta$ (TGF $\beta$), basic fibroblast growth factor (BFGF) and endothelial cell growth supplement in combination with heparin. None of the above-mentioned substances could, however, be used successfully in vivo.

Bacterial sepsis initiated by the over liberation of bacterial endotoxins (LPS) is a life threatening condition in which changes in coagulation and fibrinolysis initiated by LPS produce intervascular clotting and, in turn, organ failure. it is thought that LPS operates upon endothelial cells in which the expression of tissue factor (TF) and PAI-1 are increased.

To date there is no satisfactory direct treatment of patients which can cure intervascular clotting induced by LPS and efforts to deal with the systems triggered by LPS like, for example, hypercoagulation, are on the one hand limited to heparin and on the other by treatment of the bacterial sepsis with antibiotics. In China, the Chinese herbal drug Panax notoginseng or triterpensaponins have been used by traditional Chinese doctors to relieve pain and treat cardiovascular heart disease and stasis for thousands of years.

Indeed for example in L. Zechmeister, Progress in the Chemistry of Organic Natural Products, Vol. 46,Springer-Verlag, Vienna, N.Y., 1984,in the chapter on "Saponins of Ginseng and Related Plants", the characteristics of Panax notoginseng as a tonic, a haemostat, a coronary therapeutic and an antihaemorrhagic have been described. Also there is an indication in Chemical Abstracts 119, 85 683 as to the antihaemorrhagic effect of Panax notoginseng and in the Japanese Patent Abstracts JP Kokai No. 55-127 317,as to the antifibrinolytic effect and in JP Kokai No. 63-198 609 as to the blood flow promoting effect of Panax notoginseng. In none of these previous references, however, is the clot dissolving effect of Panax notoginseng or the saponins isolated therefrom described. This clot dissolving effect of Panax notoginseng or of astragaloside has thus not heretofore been described anywhere. Generally there are hardly any therapeutically usable substances known which increase endogenous fibrinolytic activity or which are effective against clot formation and the antifibrinolytic activity of endotoxins.

SUMMARY OF THE INVENTION

The use of substances to increase the fibrinolytic capacity and to directly block the LPS effect is described here for the first time. The subject of this invention is the use of triterpensaponins, like notoginsenoside R1 (NR1) and/or astragaloside (ASIV) or substances with related chemical structure, which differ from triterpensaponin only by their side chain residues and/or the glycosylation, either in the form of pure substances or as mixtures thereof, for producing medicaments which can be used to treat patients either parenterally or orally in the form of solutions or tablets or capsules, to increase fibrinolytic capacity, prevent cardiovascular diseases and inhibit endotoxin effects as, for example, in septic shock.

EXAMPLES

In all examples the following materials and methods are used.

Chemically pure notoginsenoside R1 (NR1) or chemically pure astragaloside ASIV was purchased from the National Institute for the Control of Pharmaceutical and Biological Products (Beijing, China). NR1 or astragaloside ASIV are substances with the following formulae:

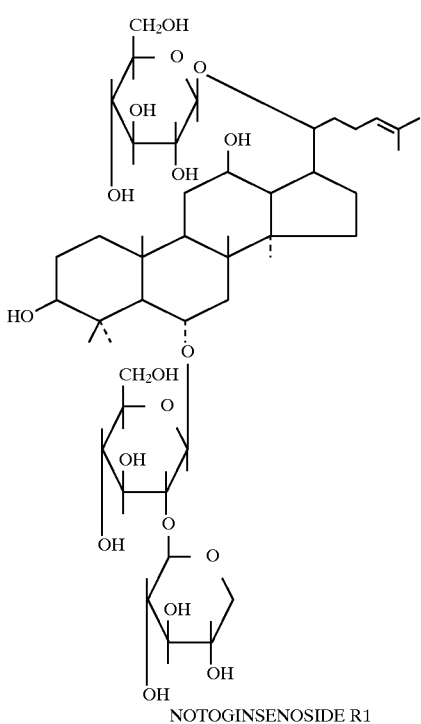

NOTOGINSENOSIDE R1

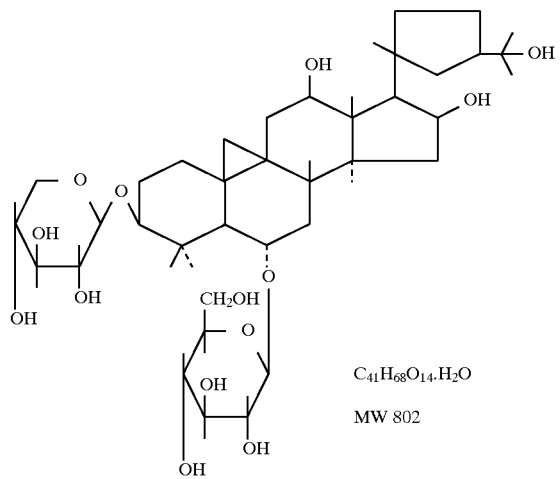

$C_{41}H_{68}O_{14} \cdot H_2O$

MW 802

ASTRAGALOSIDE IV

NR1 or ASIV are dissolved an incubation medium and diluted to achieve a final concentration of 0.01 to 100 μg/ml. Lipopolysaccharide (Escherechia coli lipopolysaccharide, Sero type 026:B6 prepared by phenol extraction) was obtained from Sigma (St. Louis, Mo., USA). A solution with a concentration of 1 mg/ml in distilled water was stored at −70° C. Morpholinopropanesulfonic acid (Serva, Germany), guanidine thiocyanate (Fluka, Switzerland), piperazine-N, N'-bis(2-ethane-sulfonic acid) (PIPES; Sigma), Seakem LE agarose (FMC Bioproducts, Me., USA), dCTP [Aloha-32P] (ICN Radiochemicals, Calif., USA) were obtained from the indicated firms. The remaining materials which are described in the methods have been specified in detail in the corresponding citations.

Cell Culture

Endothelial cells were isolated from fresh human umbilical cord veins by collagenase (Sigma) by a technique similar to the protocol of Jaffe et al., J. Clin Invest 1973; 52: 2745–56. Cells from 4–6 umbilical cords were pooled and plated in 75 cm² tissue culture flasks (Costar, Mass., USA) which were coated with 1% calf hide gelatin (Sigma). The cells were cultivated to confluence at 37° C. in a water vapor saturated atmosphere of 95% air and 5% $CO_2$ in medium 199 (Sigma) to which were added 20% heat inactivated supplemented calf serum (SCS; Hyclone, Utah, USA), 100 μg/ml Streptomycin, 100 IU/ml Penicillin, 250 ng/ml Fungizon, 1 mM glutamine (JHR Biosciences, Kans., USA), 2 IU/ml Heparin (Liquemin Roche; Hoffmann La Roche, Switzerland), 50 μg/ml ECGS (Technoclone, Austria). The endothelial character of the cells was confirmed by their typical cobblestone morphology which was characterized by their typical cobblestone morphology, by positive immunoflorescence with anti-Von Willebrandt Faktor VIII antibodies and by the takeup of acetylated low density lipoprotein (LDL). Primary cultures at the confluence time point were harvested with 0.05% Trypsin/0.02% EDTA (JRH Biosciences) and were plated in a split ratio of 1:3 in 75 cm² cell culture flasks. Subconfluence cells were allowed to grow until they attained confluence and were harvested during the exponential cell growth with trypsin/EDTA and were frozen in 1 ml portions of medium 199 with 10% dimethyl sulfoxide (DMS) in liquid nitrogen. For the experiments, the cells were thawed at 37° and were grown in 6-well plates (diameter 3.5 cm; Costar) in medium 199 to which SCS, ECGS and heparin were added in the above given concentrations until reaching confluence. In all experiments cells between the second and third passages were used. The cells were always fed the day before the experiment with fresh medium. All of the materials used in thee cell culture were determined to be free from endotoxin (detection limit of the test 5 pg/ml) by the Coatest Endotoxin Kit (Kabi Vitrum, Sweden).

Production of the Conditioned medium (CM) and the Extra Cellular Matrix (ECM)

Confluent cultures are washed twice with Hank's Balanced Salt solution (HBSS; Sigma) and incubated at 37° C. with 1 ml/Napf of medium 199 to which is added 1.25% SCS and 50 μg/ml ECGS and NR1 or ASIV in the indicated concentrations. After the incubation, the cell culture supernatant was collected and after centrifugation to remove cell fragments, was stored at −70° C. until used. The total cell count of the corresponding cultures was determined by trypsinizing with a hemocytometer. ECM was prepared from these or similarly treated cultures according to the method of Mimuro et al., Blood 1987; 70: 721–28.The monolayer was washed three times with cold phosphate buffered saline solution (PBS:0.01 monosodium phosphate, 0.14 m NaCl, pH 7.4) and the cellular components extracted by incubation for 10 minutes at 37° C. with PBS containing 0.5% Triton X100.

The plates were washed one further time with distilled water to remove remaining cellular components and then investigated for the presence of cell fragments microscopically. This extraction method removed visible cell components completely from the plates and the ECM was extracted by shaving into 1 ml PBS containing 0.1% SDS after 30 minutes of incubation at 37° C. The extracts were dialyzed overnight against PBS.

Tests for t-PA antigen, uPA antigen, PAI-1 antigen, PAI-1 activity and t-PA PAI-1 complexes in CM, in the ECM and in plasma.

t-PA antigen, u-PA antigen, PAI-1 antigen and the concentrations of t-PA PAI-1 complexes were determined with specific commercially available enzyme linked immunosorbent assays (ELISAs) (Technoclone) according to the manufacturers instructions. The test ranges for these assays were for t-PA between 0.3 and 2.5 ng/ml, for u-PA between 0.6 and 10 ng/ml, for PAI between 1.0 and 30 ng/ml and for t-PA PAI-1 complexes between 0.2 and 20 ng/ml. The t-PA ELISA determines free t-PA and t-PA complexed with PAI-1. The u-PA ELISA determines free u-PA and t-PA complexed with PAI-1. The PAI-1 ELISA determines free, complexed and lateral PAI-1. The t-PA PAI-1 complex ELISA exclusively measures t-PA complexes. PAI-1 activity in plasma and in CM were determined by titration assay (Technoclone) in accordance with the manufacturers instructions.

Determination of Functional Activities of tPA and PAI-1

The activities of tPA and PAI-1 was analyzed after sodium dodecyl sulfate polyacrylamide gel electrophoresis (SDS-PAGE) utilizing fibrinautography (FA) and reverse fibrinautography (RFA). SDS polyacrylamide gels and buffer were fabricated in accordance with the protocol of Laemmli, Nature 1970; 227: 680–85. FA is carried out in accordance with Granelli-Piperno et al., J. Exp Med 1978; 148: 223–34. 100 µl of the corresponding samples were applied to a 10 cm long resolving gel with 10% acrylamide and a 2 cm long stacking gel with 4% acrylamide and carried out at room temperature for 16 hours or until the color front reached the bottom of the gel. After the electrophoresis, the gels were initially treated with 250 ml water containing 2.5% triton X100 (serva) for 90 minutes (the Triton solution was changed after 45 minutes) to neutralize the SDS and then the gel was placed on a fibrin-agar-indicator film containing 1.5% agarose type L (Behring, Germany), 2 mg/ml plasminogen-rich fibrinogen (Organon Teknika, Holland) and 0.2 IU/ml bovinine thrombin. The gels were incubated at 37° C. in a humidified chamber and at different points in time were photographed. RFA was carried out in that the gels were applied to a fibrin film which was basically fabricated as described above but which additionally contained 0.4 IU/ml urokinase (Technoclone). The quantification of the tPA and PAI-1 activity in a given sample was obtained in that both lysis zones and lysis resistance zones were photographed on the indicator film. These zones were outlined on transparent paper and the outlined areas were cut out and weighed on an analytical balance. To identify the plasminogen activator contained in the CM of HUVECs, samples of the CM were incubated at 4° C. for 24 hours with either CNBr activated Sepharose bound monoclonal anti-tPA antibody (NPW 3 VPA; Technoclone) or monoclonal anti u-PA antibody (MPW 5 UK; Technoclone) or, as control, with Sepharose 4B (Pharmacia, Sweden). Thereafter the Sepharose was removed by centrifugation and 100 µl of the corresponding samples were analyzed by the above-described SDS-PAGE and subsequent FA.

Preparation of the cell lysate and measurement of the TF activity

HUVECs were incubated for 6 hours at 37° C. in medium 199 with LPS and/or NRI. The cells were washed 3 times with clotting buffer (130 mM NaCl, 8 mM Na-barbital and 12 mM Na-acetate, pH=7.4) and taken up in 300 µl clotting buffer by scraping. The scraped off cells were frozen and thawed 3 times. The cell lysate was checked for TF activity in a one step clotting assay. 100 µl of the cell lysate was incubated with 100 µl 20 mM $CaCl_2$ at 37° C. for 5 minutes in preheated plastic tubes in a coagulometer (H. Amelumg GmbH, Germany). The clotting was initiated by 100 µl preheated normal human citrate plasma or by the addition of Factor X deficient plasma (SIGMA). The TF activity was quantified with a standard curve (LOG-LOG PLOT) constructed with rabbit brain thromboplastin (SIGMA). 100 mU activity is defined as that which provides a coagulation time of 20 seconds in a standard test with normal human plasma. The observed coagulator activities corresponded to the TF activity because no procoagulant activity of the endothelial cells was detected when Factor X deficient plasma was used instead of normal plasma.

Quantification of the t-PA, PAI-1,TF mRNA quantities by Northern Blot Analysis.

The total cellular RNA is isolated from endothelial cells by acid quandine thiocyanate-phenol chloroform extraction as described by Chomzynski und Sacchi, Anal Biochem 1987; 162: 156–9. The RNA precipitate was resuspended in 50 µl 0.5% SDS and the concentration fixed at 260 nm. For the Northern Blot Analysis the RNA samples were subjected to electrophorese in 1.2% agarose gel and the fractionated DNA was transferred to a Duralon-UV ™ membrane (Stratagene, Calif., USA) by the capillary effect. The RNA blots were introduced into seal-a-meal bags and prehybridized in 50 mM PIPES, 100 mM NaCl, 50 mM Na phosphate, 1 mM EDTA containing 5% SDS for at least 3 hours at 57° C. The prehybridization buffer was discarded and replaced by fresh prehyberization buffer with $10^6$ cpm/ml of $^{32}P$ marked cDNA probe for either human t-PA, human PA1, human TF or rat glyceryl aldehyde-3-phosphate dehydrogenase which is used as an internal standard. The CDNA fragments were radioactively marked with a Random Prime DNA labelling kit (Boehringer Manneheim, Germany).

Animal Experiments

In these studies exclusively male Balb C Mice (18–30 gm body weight) were used. All experiments were carried out under ether anesthesia. The mice were injected intravenously via the tail vein with LPS (10 ng/g) and/or NR1 (1 µg/g) in a volume of 5 µg/l. At the times specified, blood specimens were obtained and anti-coagulated with sodium citrate (0.13M final concentration). Thrombocyte-free plasma was prepared by centrifugation at 2500 g for 30 minutes at 4° C. and stored at −70° C. until tested.

Dispensing of NR1 Containing Extracts to Humans

A notoginseng R1 (NR1) containing extract was administered to six healthy volunteers in a time interval of 24 hours 4×100 mg-equivalent. Blood was taken directly prior to the first administration and directly after the last administration. In these blood samples, corresponding to the above given methods, the tissue plasminogen activator inhibitor I (PAI-1) antigen, tissue plasminogen antigen (tPA) and urokinase plasminogen activator (u-PA) antigen were determined.

Statistical Analysis

The results are reported as mean ± standard deviation. An unpaired Student's t-test was used to determine significance.

BRIEF DESCRIPTION OF THE DRAWING

FIG. 7 is a bar graph illustrating the up-regulation of PAI-1 antigen measured after exposure of HUVECs to bacterial endotoxins (LPS) (1 µg/ml) for 12 hours antagonized by simultaneous treatment with various concentrations of NR1.

FIG. 11 is a set of two autoradiograms obtained by Northern Blot Analysis measuring TF mRNA and GAPDH mRNA. FIG. 11 also includes a bar graph showing the effect on TF mRNA of NR1, LPS and NR1 and LPS.

FIG. 14 also includes a bar graph showing the effect of administering ASIV to HUVECs over a period of time on the mRNA of tPA and PAI-1.

FIG. 17 is a series of two autoradiograms obtained by Northern Blot Analysis measuring TF and GAPDH mRNA. FIG. 17 also includes a bar graph showing the effect of administering ASIV, LPS and ASIV on TF MRNA in HUVECs.

FIG. 18 is a set of bar graphs showing the effects of extracts containing NR1 on fibrinolytic activity (tPA activity) in humans against an untreated control.

FIG. 19 is a set of bar graphs showing the effects of extracts containing NR1 on fibrinolytic activity (uPA activity) in humans against an untreated control.

FIG. 20 is a set of bar graphs showing the effects of extracts containing NR1 on fibrinolytic activity (PAI-1 activity) in humans against an untreated control.

EXAMPLE 1

Effect of NR1 on the production of tPA, u-PA and PAI-I-cultivated human umbilical vein endothelium cells.

Effect of notoginsenoside R1 (NR1) on production of tPA antigen (Field A), tPA PAI-1 complex (Field B) and PAI-1 antigen (Field C) in cultured HUVECs (FIG. 1).

Figure 1A:
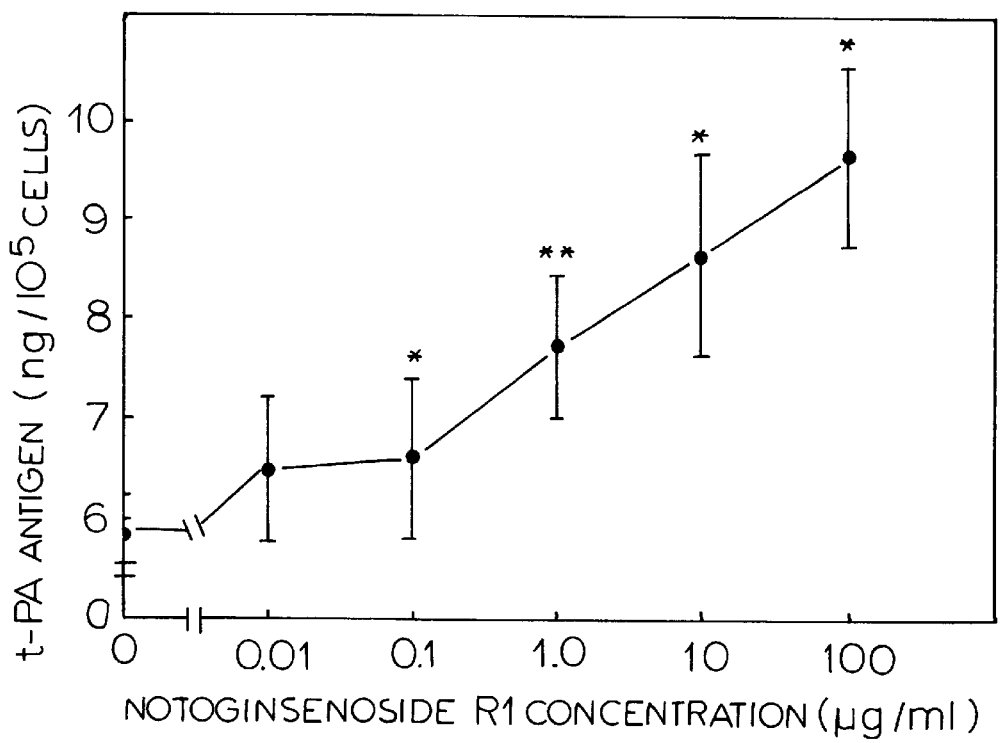
FIG. 1A is a graph showing the effect of Notoginsenoside R1 concentration in µg/ml on Tissue Plasminogen Activator (tPA) Antigen in ng/$10^5$ human umbilical vein endothelium cells (HUVEC).
Figure 1B:
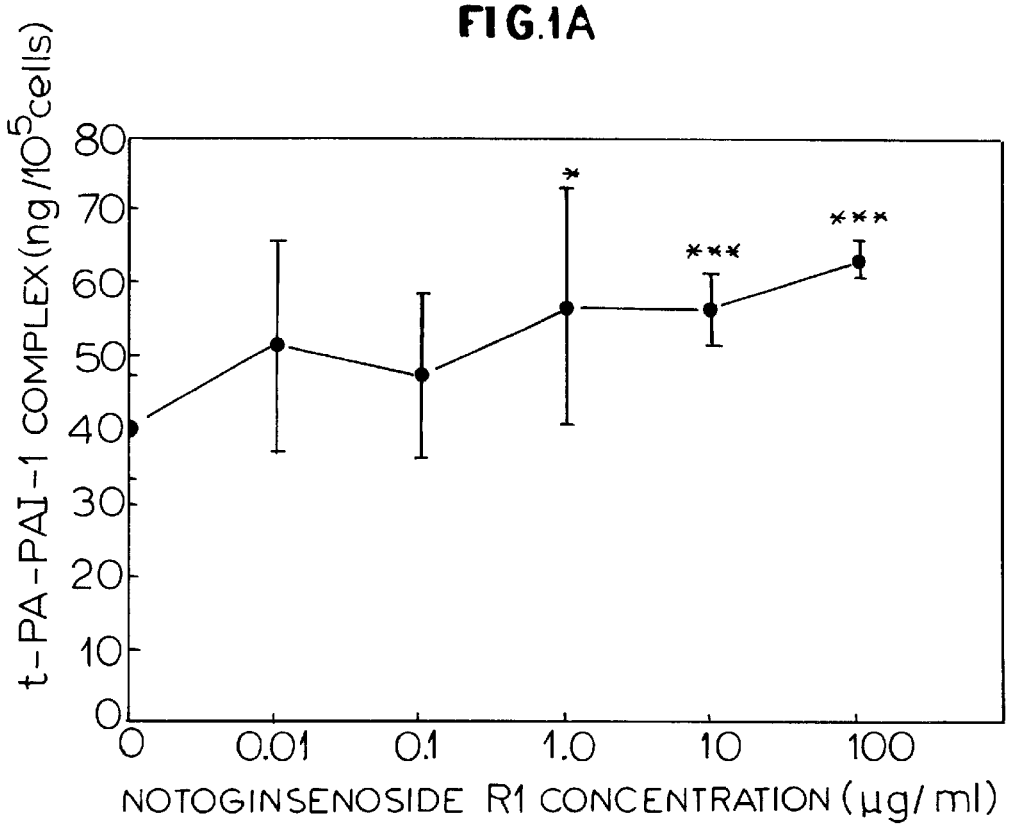
FIG. 1B is a graph showing the effect of Notoginsenoside R1 concentration in µg/ml on Tissue Plasminogen Activator-Plasminogen Activator Inhibitor (t-PA-PAI-1) Complex in ng/$10^5$ HUVECS.

HUVECs were incubated for 24 hours at different concentrations of NR1 (0.01 to 100 µg/ml) and the CM was analyzed for tPA antigen PAI-1 antigen and tPA PAI-1 complexes using the materials and methods described. The results are the average values of three experiments as carried out in triplicate. The values are given as means ± S.D. in FIG. 1. Significances are given by comparison with the controls (*p<0.05: p<0.01: *p<0.001) as indicated in FIG. 1a the treatment of HUVECs with increasing doses of NR1 for 24 hours gives rise to a dose dependent increase in the tPA antigens in the CM of such treated cells: maximum effects were reached with 100 µg/ml NR1 (100 mg/ml NR1: 9.6±0.7 ng/10$^5$ cells/24 hour; controls: 5.8±0.4 ng/10$^5$/24 hours; n=9,p<0.05). As has been indicated in FIG. 1B, the tPA PAI-1 complexes in CM increase in a similar way in the presence of increasing concentrations of NR1 (100 µg/ml NR1: 63.5±2.6 ng/10$^5$ cells/24 hours; controls:40.2±7 ng/10$^5$ cells/24 hours/n=9 p<0.01).

Figure 2:
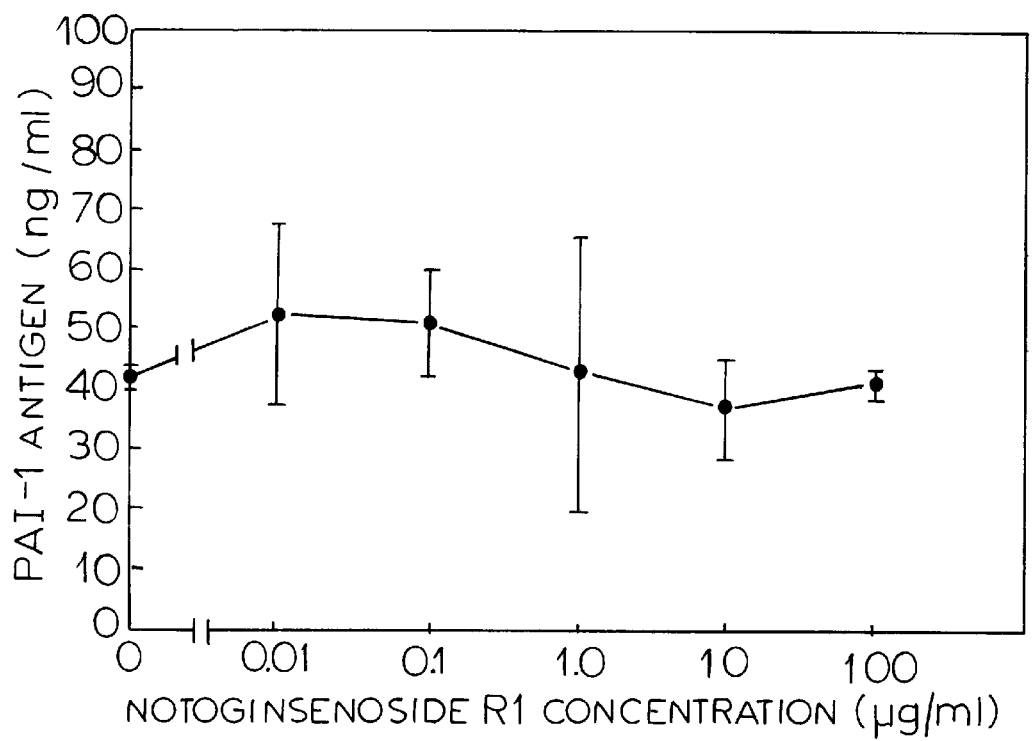
FIG. 2 is a graph showing the effect of Notoginsenoside R1 concentration in µg/ml on PAI-1 concentration in µg/$10^5$ HUVECs.

Effect of notoginsenoside (NR1) on the PAI-1 antigen production in the ECM of cultured HUVECs (FIG. 2)

Figure 1C:
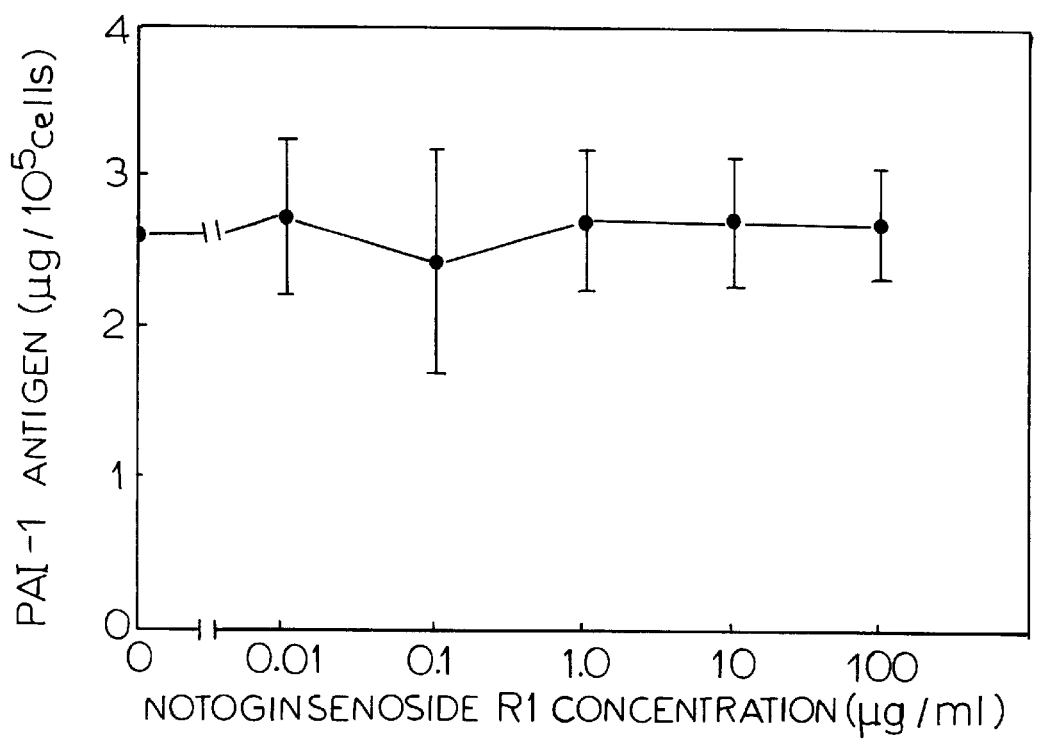
FIG. 1C is a graph showing the effect of Notoginsenoside R1 concentration in µg/ml on Plasminogen Activator Inhibitor (PAI-1) in µg/$10^5$ HUVECs.

HUVECs are incubated for 24 hours with different concentrations of NR1 (0.01–100 µg/ml). The ECM was investigated using the materials and methods described, after recovery and on PAI-1 antigen. The values are means ±SD from 6 independent wells. PAI-1 antigen in CM and in the ECM of NR1 treated HUVECs not significantly altered by comparison to the controls (Cm: 100 µg NR1/ml: 2.92±0.32 µg/10$^5$ cells/24 hours; control: 2.78±0.45 µg/10$^5$ cells/24 hours; n=9. ECM=100 µg.ml NR1:4255±3.15 ng/ml/24 hours; control: 42.27±1.66 ng/ml/n=6). (FIG. 1C, FIG. 2).

Figure 3A:
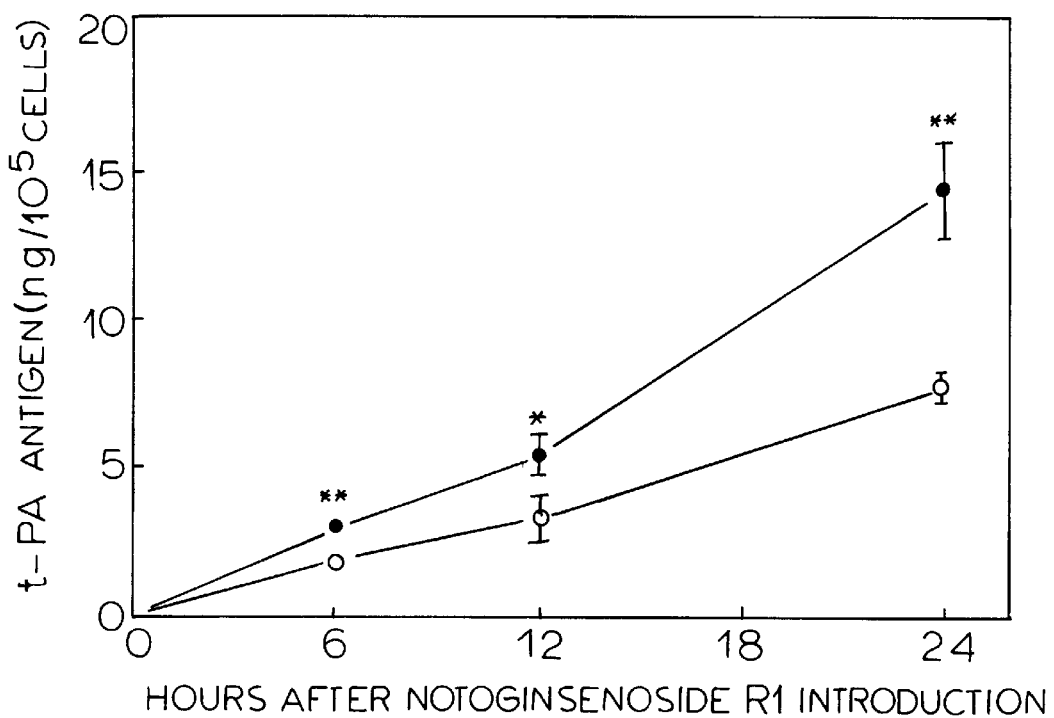
FIG. 3a is a set of two graphs plotting hours after administering Notogenoside R1 (NR1) or an inert control to HUVECs versus t-PA Antigen Concentration in (ng/10$^5$ HUVECS). The top graph shows the t-PA Antigen concentration after administration of NR1 and the bottom graph shows the t-PA Antigen Concentration after administration of the control.
Figure 3B:
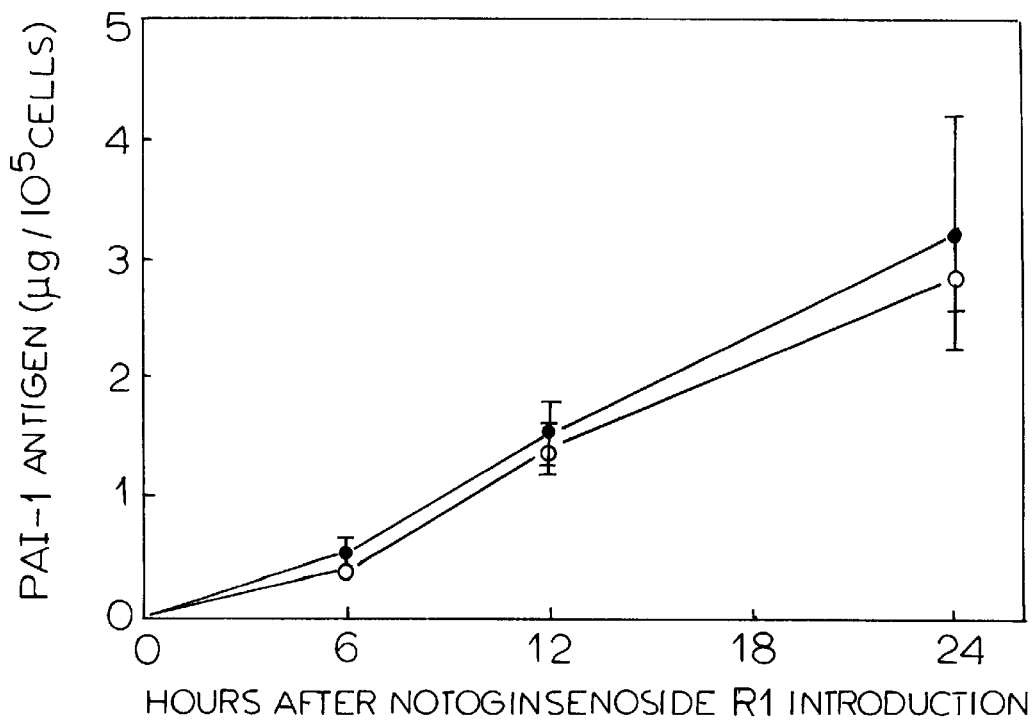
FIG. 3b is a set of two graphs plotting hours after administering Notogenoside R1 (NR1) or an inert control to HUVECs versus PAI-1 Antigen Concentration in (ng/10$^5$ HUVECs). The top graph shows the PAI-1 Antigen Concentration after administration of NR1 and the bottom graph shows the PAI-1 Antigen Concentration after administration of the control.

Time course of tPA antigen (Field A) and PAI-1 Antigen (Field B) Production of Cultured HUVECs After Treatment with Notoginsenoside (NR1) (FIG. 3)

HUVECs are incubated for the indicated time periods in the absence (open circles) or presence of 100 µg/ml NR1 (full circles). At the indicated times, the corresponding CM was harvested and using the materials and methods described were tested for tPA antigen and PAI-1 antigen. The results are given in terms of the means of 3 experiments as carried out in triplicate. The values are given as mean values ±S.D., *p<0.05; **p<0.01. As shown in FIG. 3 the tPA antigen increases in CM with a time deficiency on HUVECs which are treated for 6, 12 or 24 hours with 100 µg/ml NR1 in comparison to the control. Whereas the PAI-1 antigen in the CM of cells treated in this manner was not significantly changed.

The notoginsenoside R1 affects the u-PA antigen secretion of cultured HUVECs. When the CM harvested from HUVECs which were incubated in the presence of 100 µg/ml NR1 on u-PA antigen, a significant change is seen in the amount of the u-PA antigen product in these cells by comparison to cm from HUVECs which is cultured under control conditions (100 μg/ml NR1: 2.9±0.6 ng/$10^6$ cells per 24 hours).

EXAMPLE 2
Effect of NR1 on the tPA and PAI-1 Activity in Cultured Human Umbilical Vein Endothelial Cells Notoginsenoside R1 increases tPA activity and reduces the PAI-1 activity of cultured HUVECs.

Figure 4:
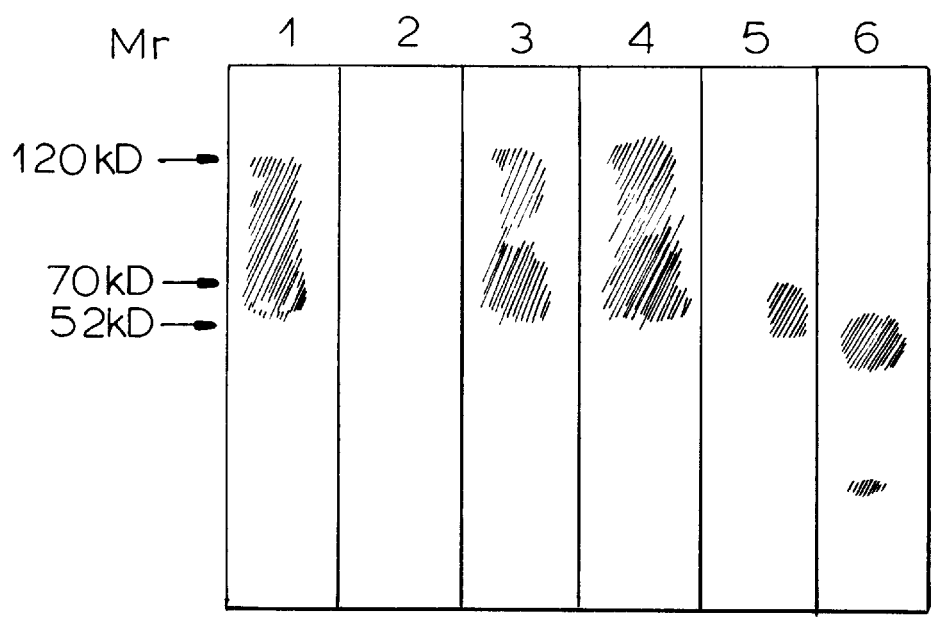
FIG. 4 is a series of six fibrinautography runs on HUVECs cell matrix (CM) samples.

Fibrinautography (FA) of HUVECs CM samples: (FIG. 4)

CM from HUVECs is collected after 24 hours and is harvested with SDS PAGE and subsequent FA as described under materials and methods. Lane 1: untreated CM from HUVECs; Lane 2: CM from HUVECs which has been preincubated on Sepharose coupled monoclonal anti-t-pA antibodies; Lane 3 CM from HUVECs which has been preincubated with Sepharose coupled monoclonyl anti u-PA antibodies; Lane 4: cm from HUVECs that has been preincubated with Sepharose 4B; Lane 5: purified human tPA; Lane 6: purified human uPA.

When CM recovered from HUVECs which have been incubated for 24 hours under control conditions with SDS-PAGE and are analyzed by FA, it is found that there are two dominant lysis zones with an apparent molecular weight of 70,000 and 120,000. That lysis zones could be depleted by preincubation with monoclonal anti-t-PA antibodies but could not be removed by preincubation with monoclonal anti u-PA antibodies (FIG. 4). Therefore, it has been concluded that the lysis zone at 70 kDa was caused by free t-PA and the high molecular lysis zone stemmed from t-PA complexed with PAI-1.

Figure 5A:
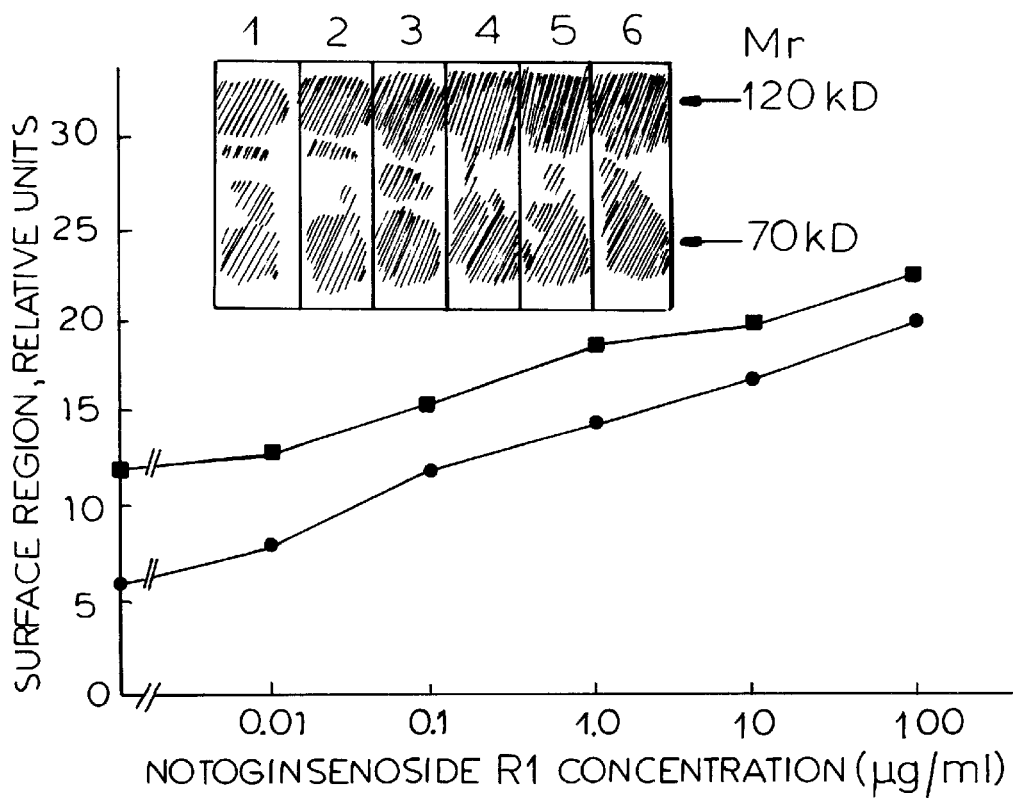
FIG. 5A is a combination of two graph and fibrinautography (FA) data where concentration of NR1 is plotted against relative units of a surface region.
Figure 5B:
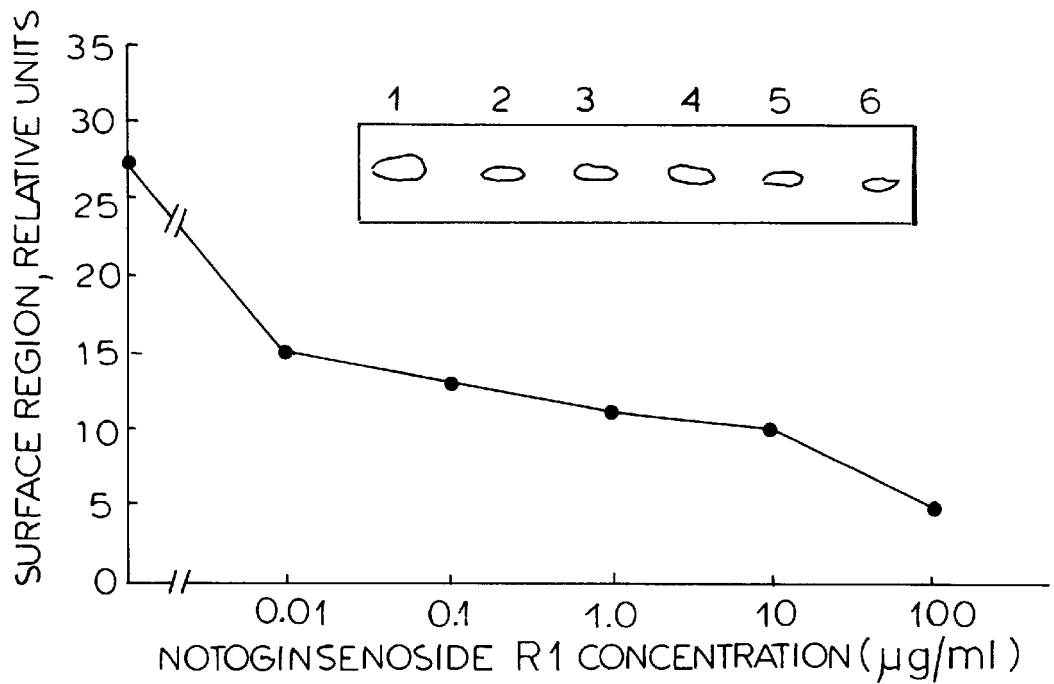
FIG. 5B is a combination of a graph and reverse fibrinautography (RFA) data where concentration of NR1 is plotted against relative units of a surface region.

Effect of Notoginsenoside R1 (NR1) on the tPA activity and on the activity associated with the tPA PAI-1 complex (Field A) and on the PAI-1 activity (Field B) in cultured HUVECs after analysis with fibrinautography (FA) and reverse fibrinautography (RFA) (FIG. 5).

After the incubation of confluent HUVECs for 24 hours with different concentrations of (NR1) (0.001–100 μg/ml), the cm was subjected to SDS-PAGE and subsequent FA or RFA as described under materials and methods. The lysis zones and the lysis resistance zones in this FIG. were transferred to transparent paper, cut out and weighed on an analytical balance. The weight of this transparent paper was plotted against the concentration of (NR1) (lower field). The data represent results of one of three separate experiments which indicate similar results. Lane 1: Control; Lane 2: 0.01 μg/ml NR1; Lane 3: 0.1 μg/ml NR1; Lane 4: 1.0 μg/ml NR1; Lane 5: 10 μg/ml NR1; Lane 100 μg/ml NR1. When the CM from HUVECs is cultured with or without increasing concentrations of NR1 for 24 hours, and was analyzed with FA or RFA, a dose dependent increase in the size of the lysis zones is detected while the sizes of the lysis resistant zones decrease with the increasing amounts of NR1 (FIG. 5A and B). When the size of the lysis zones or the lysis resistance zones is quantified as described under materials and methods an up to 3-fold increase in the tPA-dependent lysis is established in contrast to the PAI-1 dependent lysis resistance which is reduced to 20% in the presence of 100 μg/ml NR1 as compared to control (FIG. 5A and B).

Figure 6:
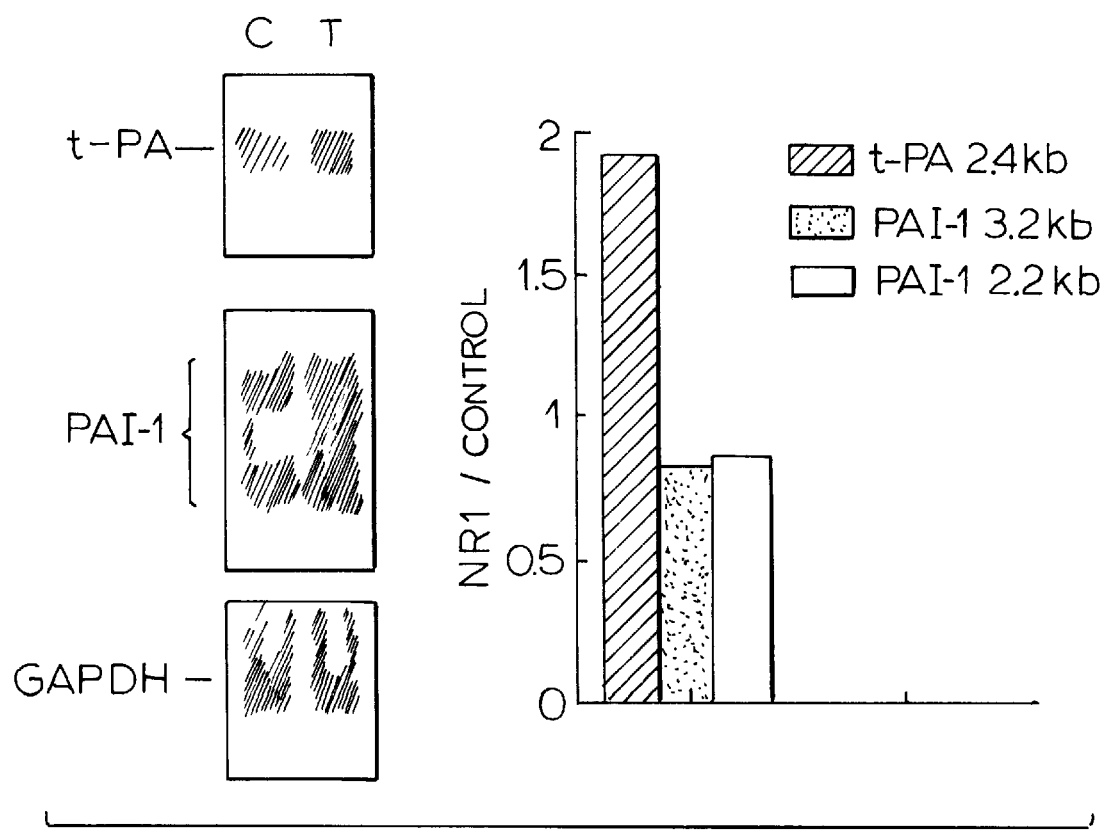
FIG. 6 includes a set of three autoradiograms obtained by Northern Blot Analysis of RNA extracts for untreated and NR1 treated HUVECs using $^{32}$P marked CDNA probes for tPA, PAI-1 and GAPDH mRNA. Also included is a bar graph interpreting the Northern Blot data concerning the effect of NR1 on HUVEC expression of tPA and PAI-1.

EXAMPLE 3
Effect of NR1 on the t-PA and PAI-1 mRNA-Cultured Human Umbilical Vein Endothelial Cells Effect of notoginsenoside R1 (NR1) upon tPA and PAI-1 mNRA expression in HUVECs (FIG. 6).

Confluent HUVECs were incubated for 12 hours in the absence or in the presence of NR1 (100 μg/ml). The Northern Blot Analysis of the RNA extracts for untreated and NR1 treated HUVECs was effected using $^{32}$p marked cDNA probes for tPA, PAI-1 and GAPDH mRNA. The intensities of the bands of the autoradio diagram were evaluated with the aid of densitometry and the specific mRNA was normalized against GAPDH mRNA for the specific mRNA for tPA or PAI-1 to take into account differences in the loading. The signal intensities were compared as the ratio of the signals with NR1 treated HUVECs by comparison to signals from untreated control cells. These data include the results of two independent experiments which showed similar results. As illustrated in FIG. 6, the stimulating effect of NR1 on the secretion of tPA in HUVECs is also reflected in the level of the specific mRNA expression. The tPA specific mRNA increases up to a two-fold value in 12 hours with 100 μg/ml NR1 treated HUVECs whereas the PAI-1 specific mNRA expression was not controlled by NR1 (3.2 kb:82% of the control, 2.2 kb:86% of the control). When North Blot experiments were carried out in the presence of 10 μg/ml cyclohexamide, the stimulating effect of NR1 on the tPA specific mRNA was inhibited (data not shown).

EXAMPLE 4
Effects of NR1 on the up-regulation of PAI-1 antigen, activity and PAI-1 MRNA in vitro by endotoxin.

Figure 8:
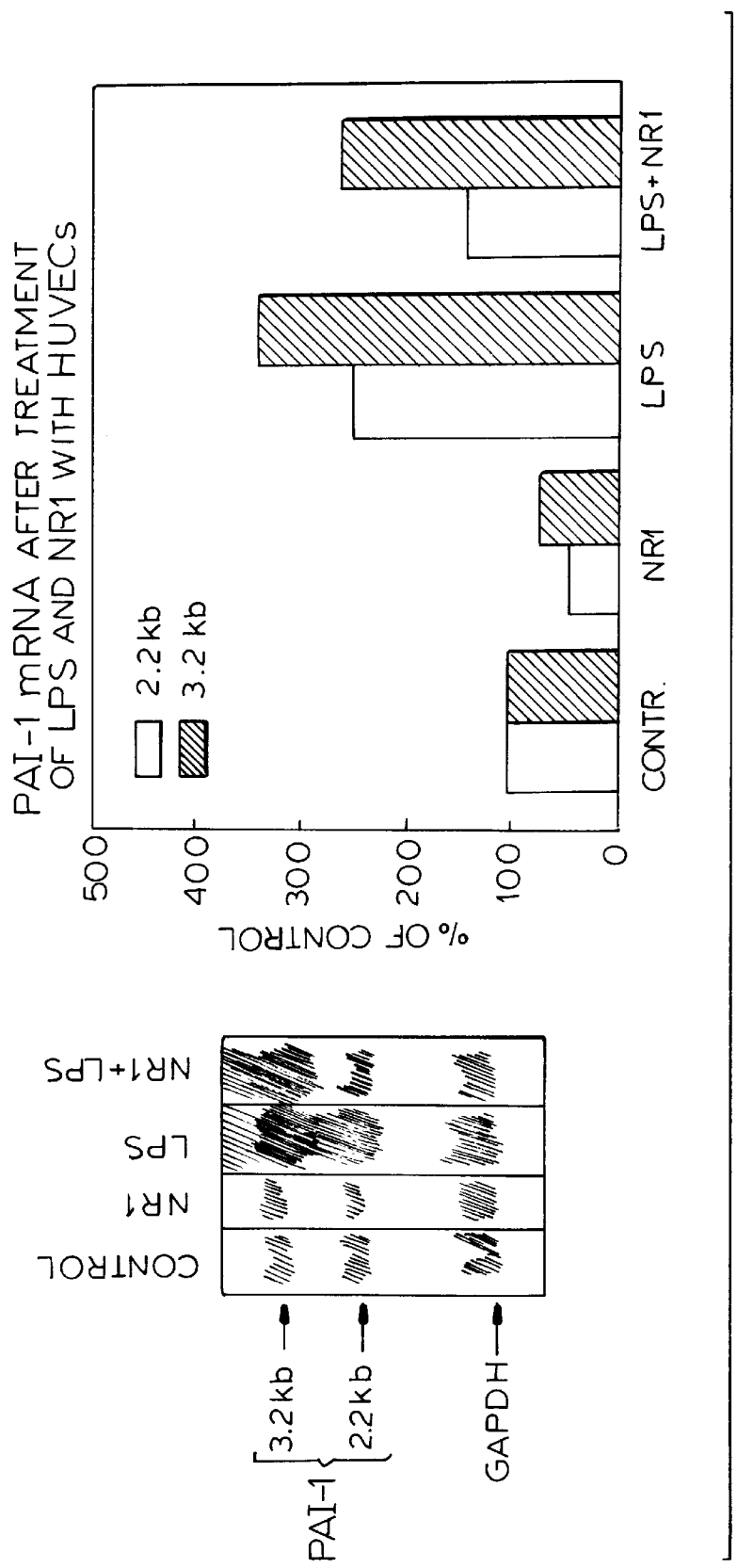
FIG. 8 is an autoradiogram obtained by Northern Blot Analysis of RNA extracts treated with LPS, NR1 and both LPS and NR1 to show the effects of LPS, NR1, and LPS and NR1 on PAI-1 activity. Also included is a bar graph interpreting the data concerning the effect on PAI-1 activity.

As illustrated in FIG. 7, the up-regulation of PAI-1 antigen measured after exposure of cells to LPS (1 μg/ml) for 12 hours is antagonized by simultaneous treatment with various concentrations of NR1. The extent of the antagonism was dose dependent upon NR1 concentration (0.1–100 μg/ml) and the LPS induced increase in the PAI-1 antigen was significantly reduced by the co-incubation of the cells with 100 μg/ml NR1 (control cells: 347±34 ng/$10^5$ cells/12 hours, LPS treated cells: 946±42 ng/$10^5$ cells/12 hours, LPS and NR1 treated cells: 469±29 ng/$10^5$ cells/12 hours). The change in PAI-1 activity of the cells was parallel to the change in PAI-1 antigen (control cells: 5.48±0.8 μ/$10^5$ cells 12 hours, LPS treated cells: 8.22±0.18 μ/$10^5$ cells/12 hours, LPS and NR1 treated cells: 4.77±0.26 μ/$10^5$ cells/12 hours/n=6). The mRNA for PAI-1 was measured in cells which were treated with one μg/ml LPS and/or 100 μg/ml NR1. The increase induced by LPS to a two-fold amount of PAI-1 specific mRNA (3.2 kb) was reduced in the presence of both LPS and NR1 to a 1.37 fold increase (FIG. 8).

EXAMPLE 5
Effect of NR1 on the LPS induced upregulation of the PAI-1 activity in vivo.

Figure 9:
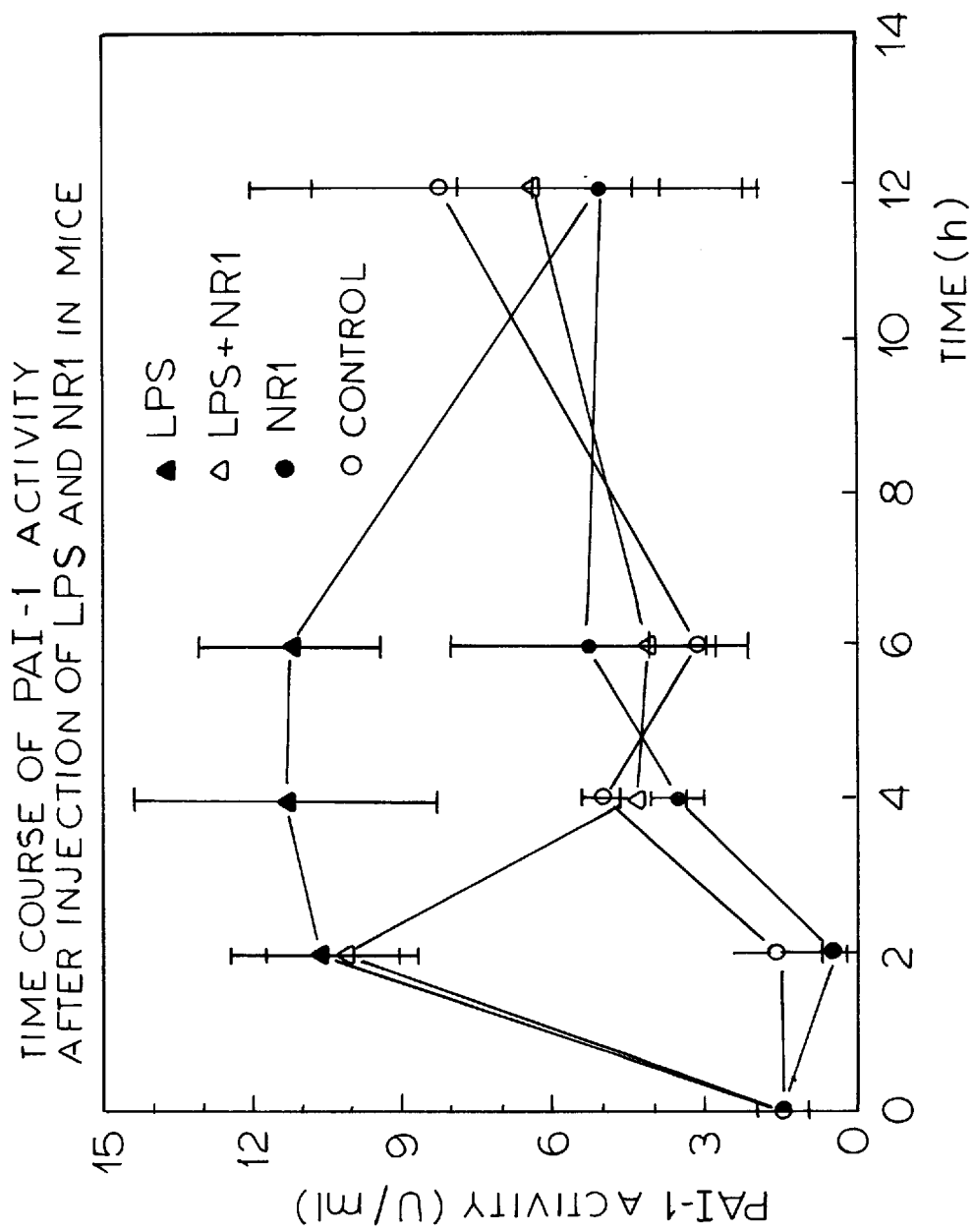
FIG. 9 is a series of line graphs plotting time against PAI-1 Activity in mice who were injected with LPS, NR1, LPS and NR1 or an inert control.

In vivo studies indicate that the injection of LPS in mice results in a rapid increase in the plasma PAI-1 activity. With an LPS dose of 10 ng/g (body weight) an increase from significant to 7 fold above the control value can be reached two hours after the injection while maximum value is reached 4 hours after injection. At a later time, the PAI-1 activity returned gradually to normal values. By contrast, the PAI-1 activity in animals treated simultaneously with LPS and NR1 (1 μg/g) returned to the control value 4 hours after the injection (LPS treated group: 11:3±3.1 U/ml, LPS and NR1 treated group: 4.3±1.0 U/ml, control group: 4.9±0.3 U/ml, n=5–8) (FIG. 9).

Figure 10:
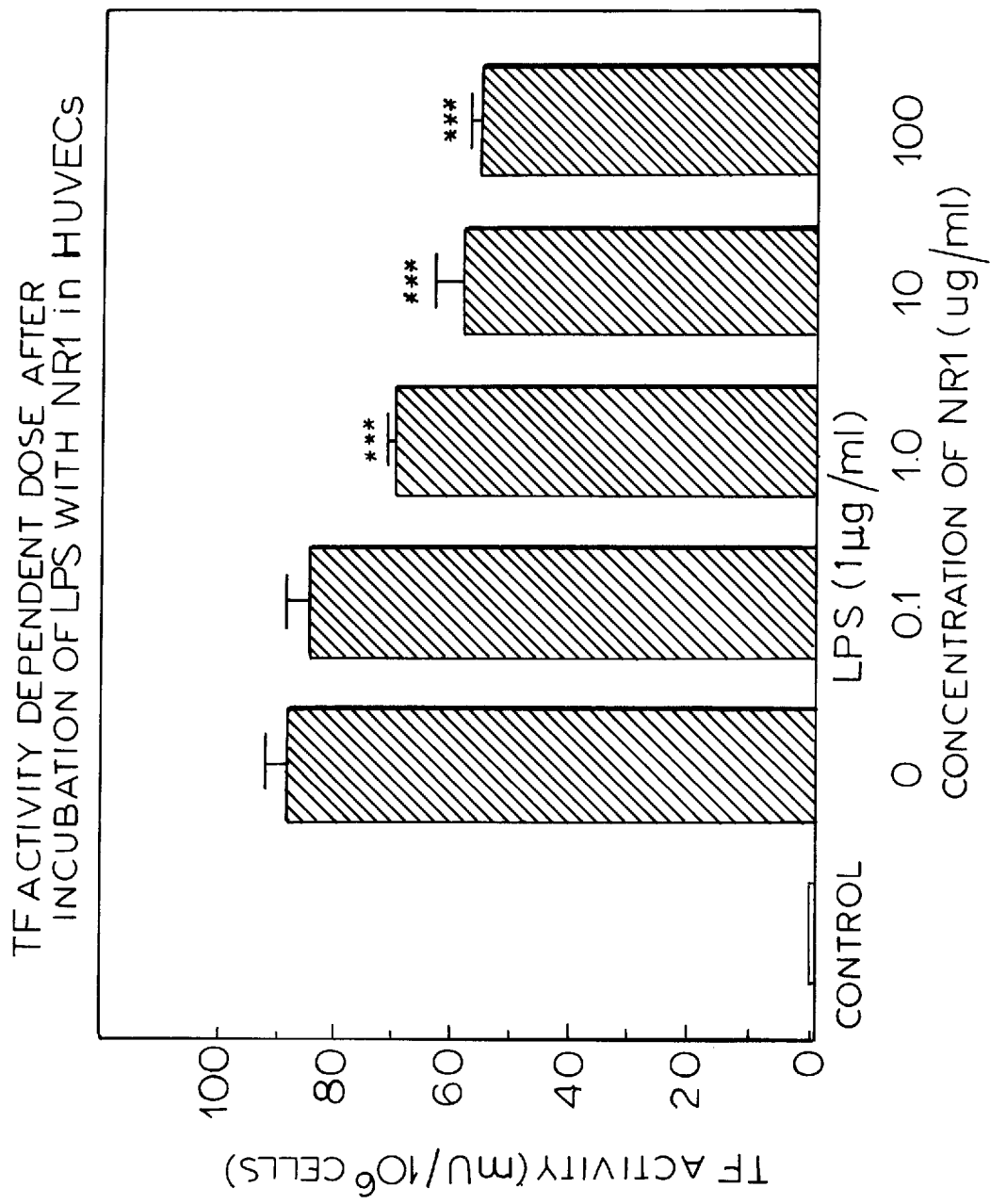
FIG. 10 is a series of bar graphs showing Tissue Factor (TF) Activity after administration to HUVECs of 1 µg/ml LPS alone and with various concentrations of NR1.

EXAMPLE 6
Effects of NR1 on the endotoxin (LPS) induced TF activity and mRNA in cultured HUVECs:

In untreated HUVECs only a very small amount of TF activity is found (0.78±0.15 mU/$10^6$ cells, n=9). The TF activity increases in HUVECs after treatment with LPS (1 μg/ml for 6 hours) to a value of 88.6±6.5 mU/$10^6$ cells (n=6). The TF activity measured in HUVEC after 6 hours of treatment with 1 μg/ml LPS is significantly antagonized by coincubation with NR1 (LPS and NR1 treated cells: 56.0±1.9 mU/10⁶ cells). The extent of the antagonism was also dose dependent with respect to NR1 concentration, whereby with 100 μg/ml MR1 an approximately 36.8 % inhibition was achieved (FIG. 10) a significant increase in the TF mRNA was observed after treatment of HUVEC with LPS which reached a 9 fold increase (2.4±3.1±3.5 kb) over control values after 2 hours. The TF mRNA values increased by LPS were antagonized in a similar way by coincubation with RN1;the TF mRNA was reduced to a 4-fold value over the control. The treatment of the cells with 100 μg/ml NR1 alone reduced the TF mRNA values to 40% of the control values (FIG. 11).

EXAMPLE 7
Effect of astragaloside (ASIV) on the antigen concentrations of tPA and PAI in human endothelial cell culture.

Figure 12:
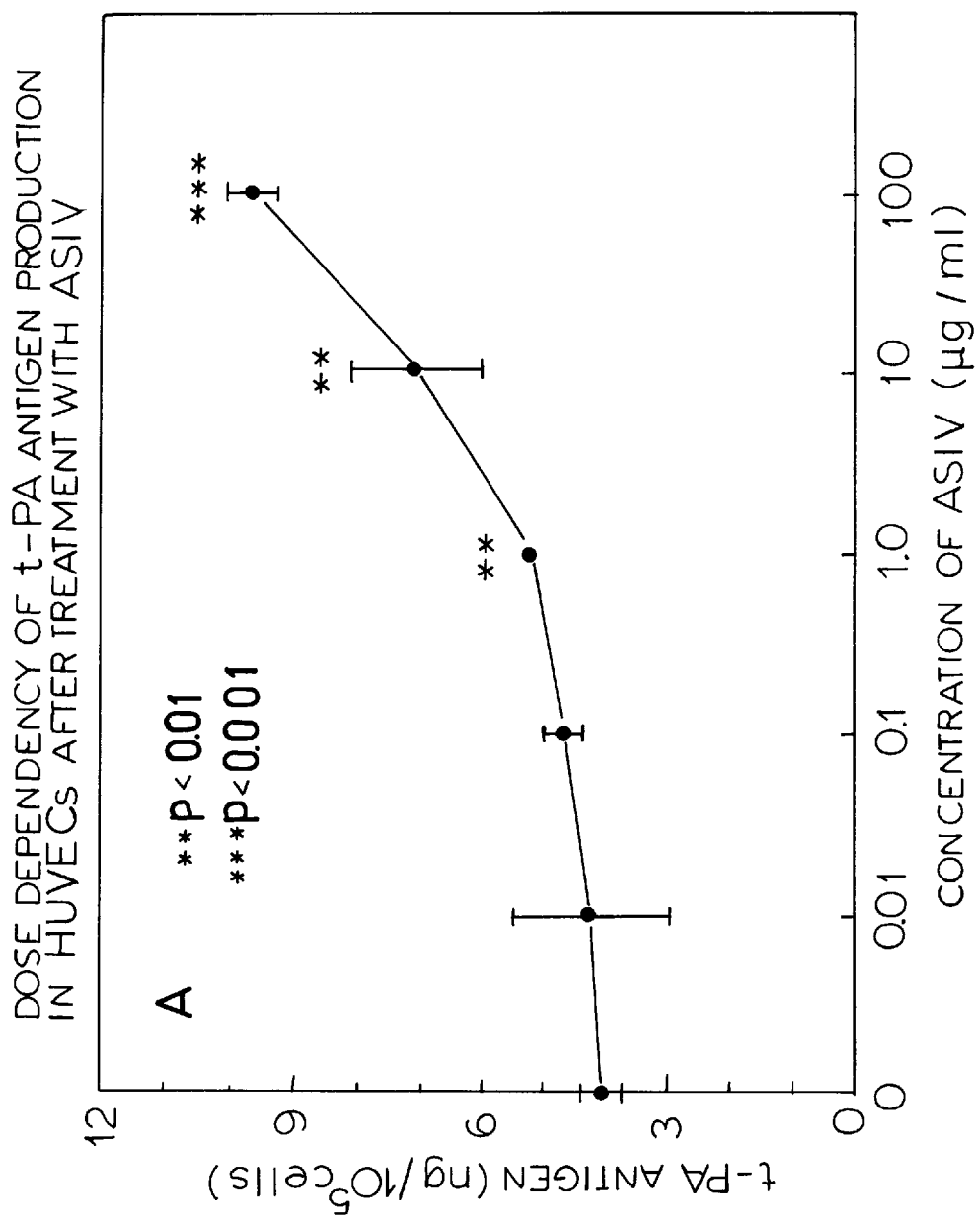
FIG. 12 is a graph plotting the concentration of astragaloside (ASIV) against tPA activity.
Figure 13:
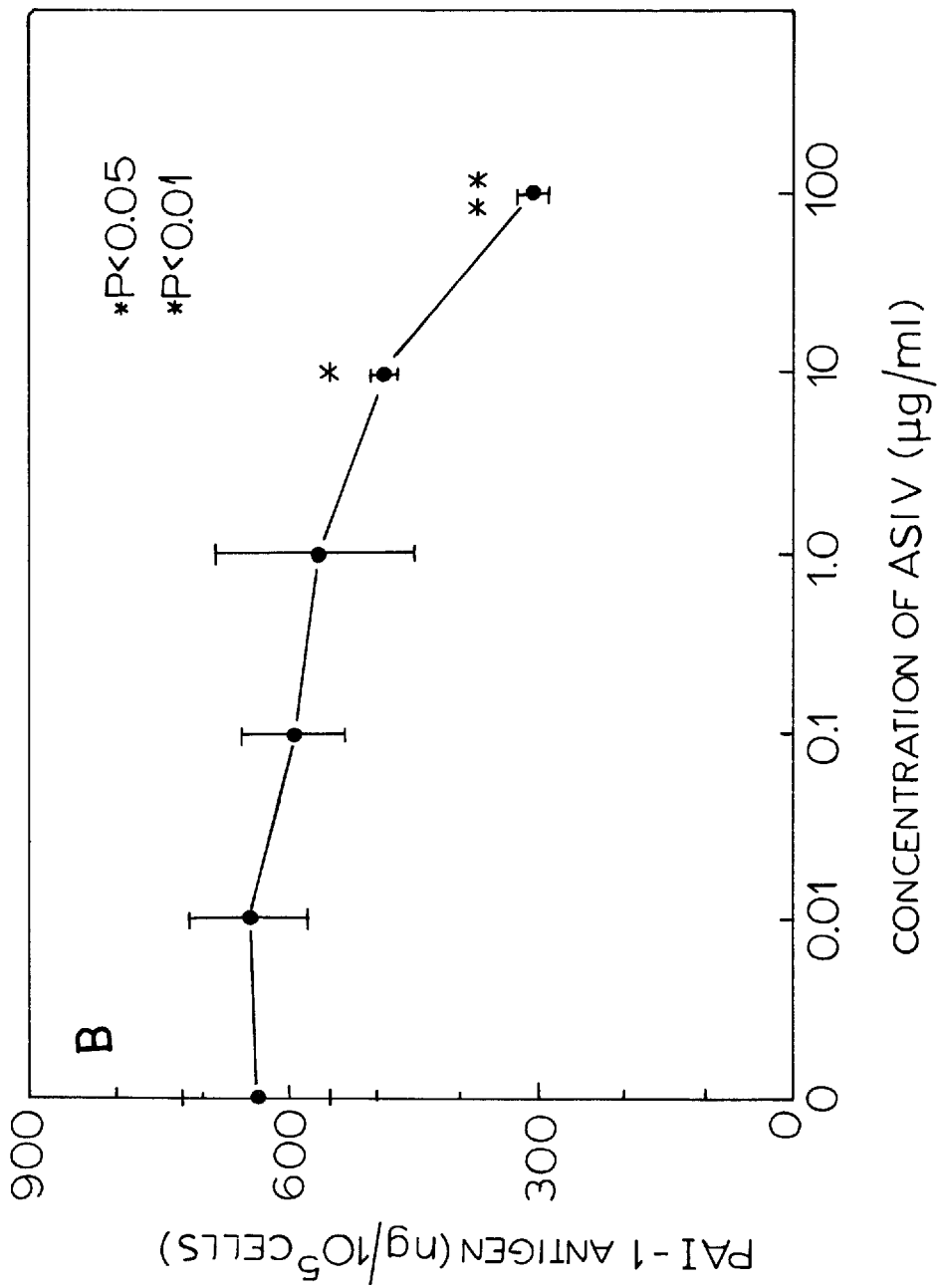
FIG. 13 is a graph plotting the concentration of astragaloside (ASIV) against PAI-1 Antigen activity.

Effect of astragaloside IV (ASIV) on tPA antigen and PAI-1 antigen production in culture HUVECs (FIGS. 12 and 13).

HUVECs were incubated for 24 hours with different concentrations of ASIV (0.01–100 μg/ml) and the CM was analyzed for tPA antigen and PAI-1 antigen as described under materials and methods. The results are the mean values of three experiments, each in triplicate. The values are the mean values ±S.D. indicated in FIGS. 12 and 13. Significances are in comparison to the control (* $p<0.05$;  $p<0.01$; * $p<0.001$). As indicated in FIG. 12, the treatment of HUVECs with increasing concentration of ASIV for 24 hours results in a dose dependent increase of the tPA antigens in the CM of such treated cells: maximum effect is reached at 100 μg/ml ASIV.

FIG. 13 shows the effect on the PAI-1 antigen production in the CM of cultured HUVECs (FIG. 13). HUVECs were incubated for 24 hours with different concentrations of ASIV (0.01–100 μg/ml). The CM was recovered as described under materials and methods and investigated for PAI-1 antigen. The values are mean values ±S.D. from three investigations carried out each in triplicate. Antigen in CM was significantly altered with ASIV treated HUVECs in comparison to the controls.

EXAMPLE 8
Effect of astragaloside on messenger ribo nucleic acid (mRNA) of tPA and PAI-1 in human endothelial cells.

Figure 14:
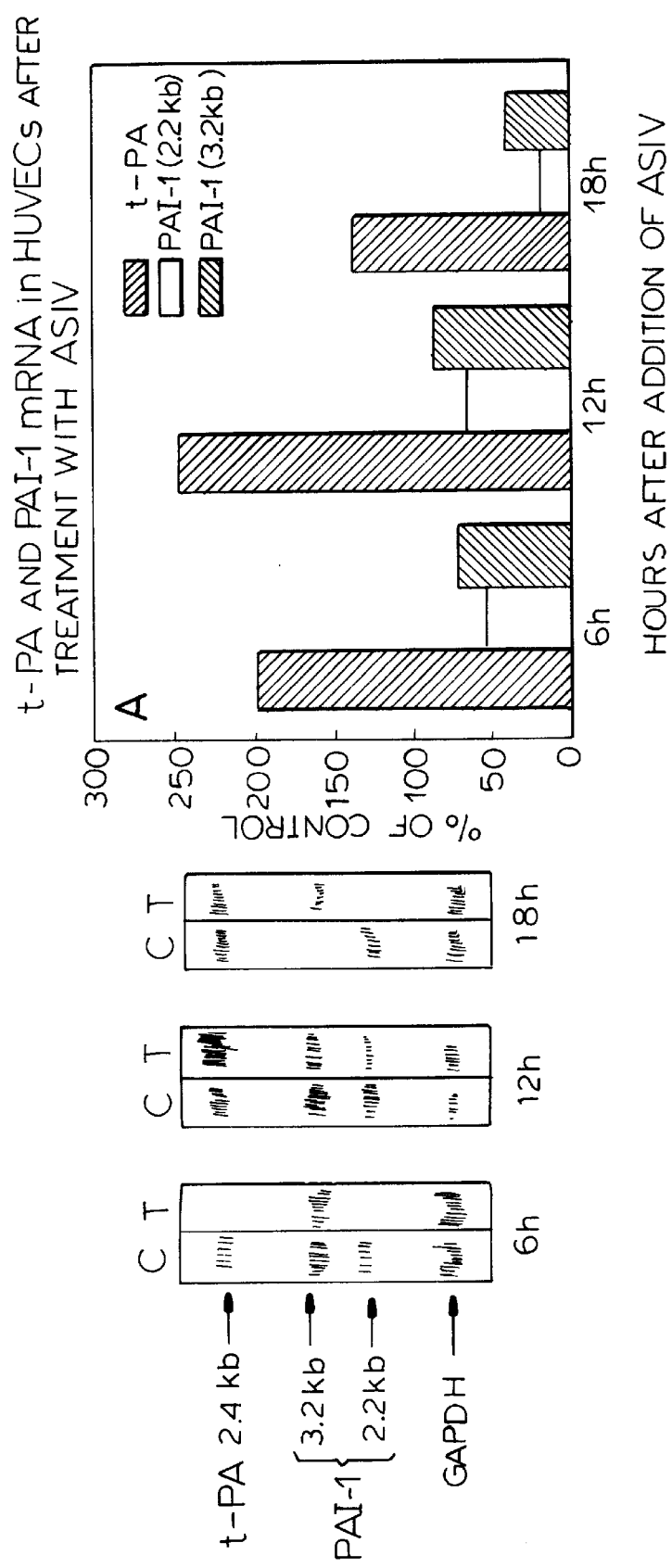
FIG. 14 is a series of three autoradiograms obtained by Northern Blot Analysis measuring tPA, PAI-1 and GAPDH mRNA.

Effect of astragaloside ASIV upon the tPA and PAI-1 mRNA expression in HUVECs: (FIG. 14)

Confluent HUVECs were incubated for 6, 12 and 24 hours in the absence or presence of ASIV (100 μg/ml) the Northern Blot Analysis of the RNA extracts from untreated and ASIV treated HUVECs was carried out with the use of 32 P marked CDNA probes for tPA, PAI-1 and GAPDH mRNA. The intensity of the bands of the autoradiogram were evaluated by densitometry and the specific mRNA for tPA or PAI-1 were normalized against GAPDH mRNA to determine differences in the loading. The signal intensities were compared as the ratios of the signals with NR1 treated HUVECs in comparison to signals from untreated control cells. These data were indicated as results of two independent experiments with similar results. As shown in FIG. 14, the stimulating effect of ASIV on the secretion of tPA and on the inhibiting effect of the secretion of PAI-1 in HUVECs is also reflected in the level of the specific mRNA expression.

EXAMPLE 9
Effect of astragaloside A IV on the PAI-1 and tissue factor expression in endotoxin treated endothelial cell cultures.

Figure 15:
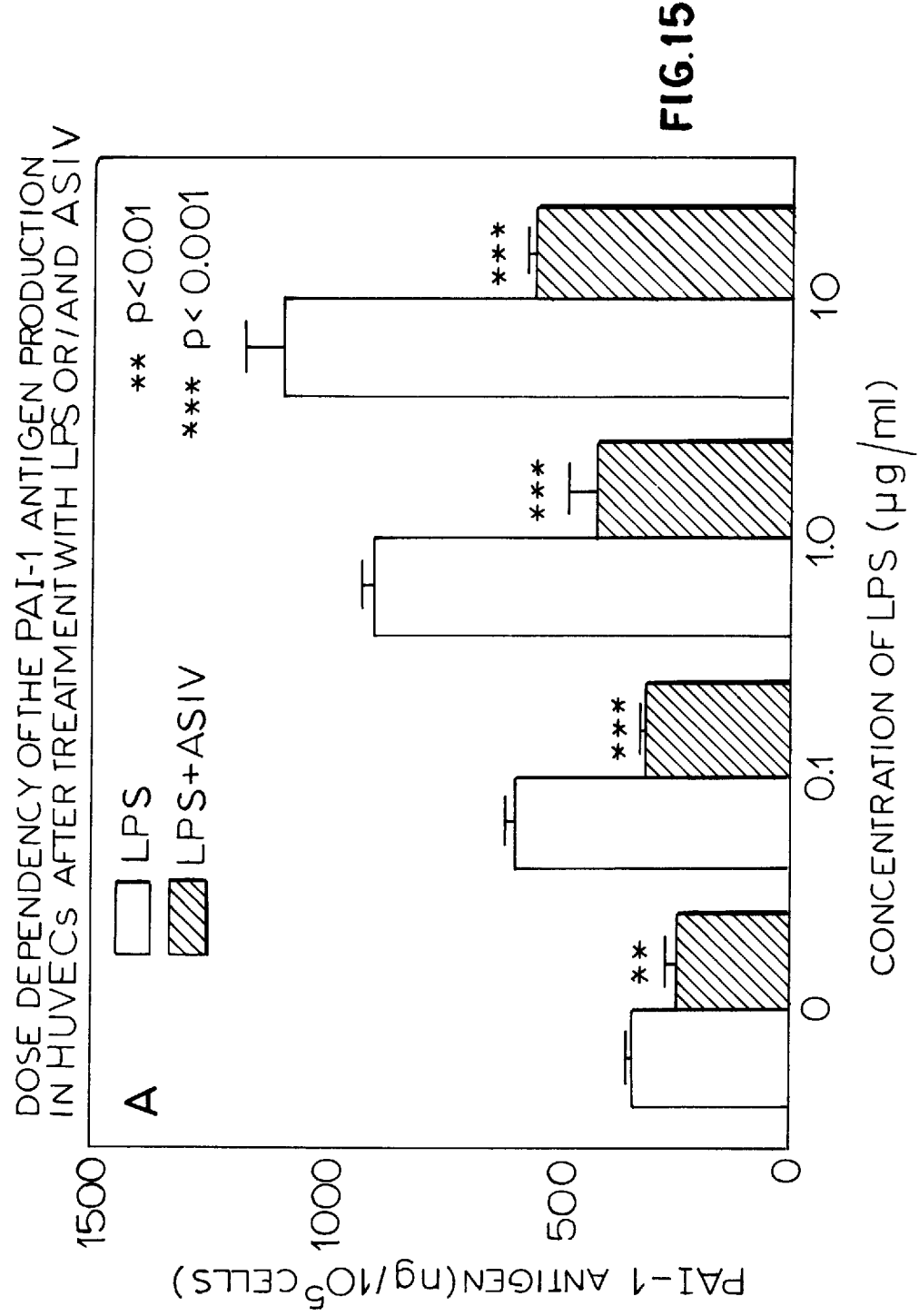
FIG. 15 is a series of bar graphs showing the effect of treating HUVECs with LPS and/or ASIV on PAI-1 antigen production.
Figure 16:
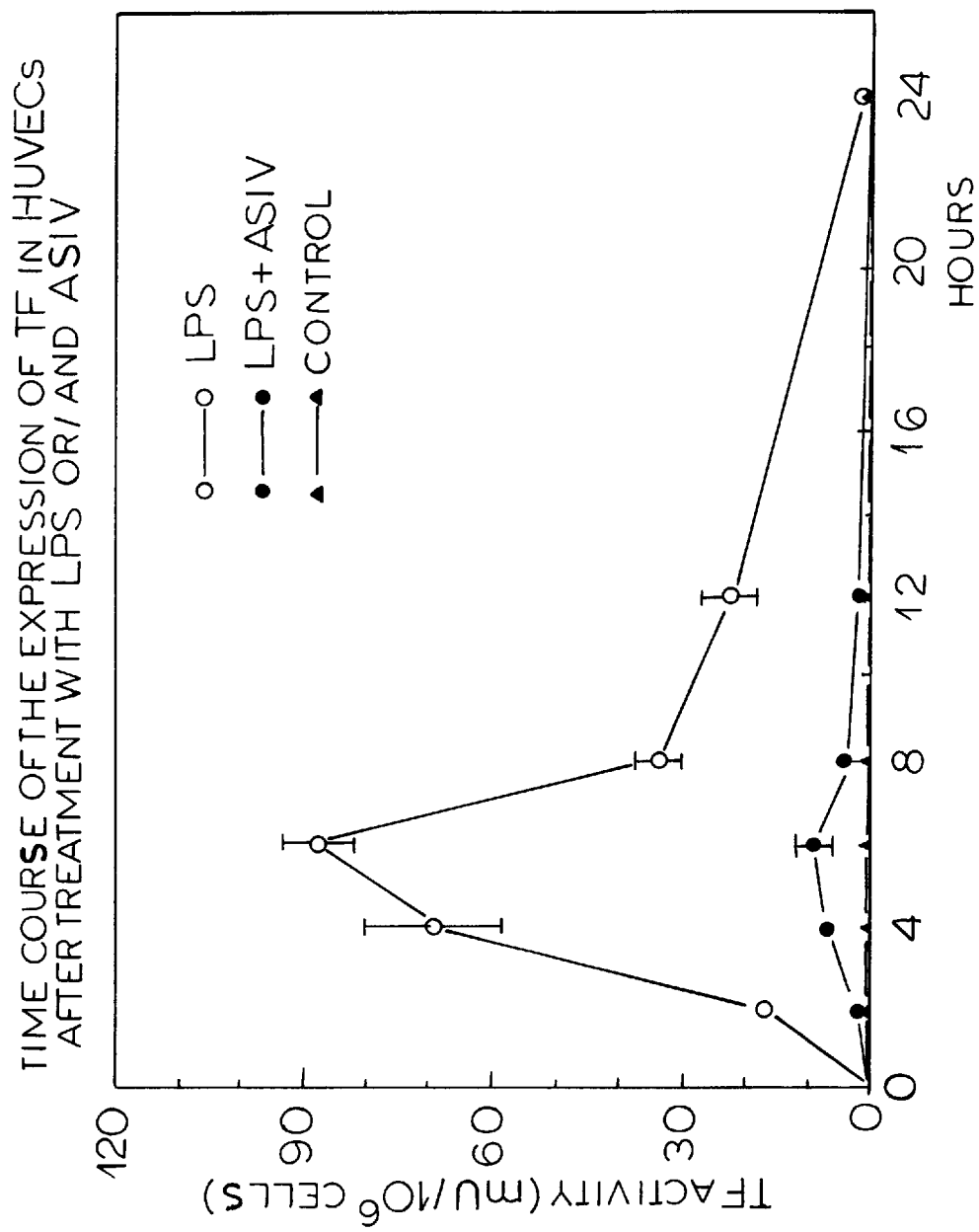
FIG. 16 is a graph plotting time against TF Activity in HUVECs after treatment with LPS and/or ASIV.

As indicated in FIG. 15, the upregulation of the PAI-1 antigen after treatment of the cells with LPS in different concentrations (0.1–10 μg/ml for 12 hours) by simultaneous treatment with ASIV is significantly reduced ( $p<0.01$; * $p<0.001$). The extent of the antagonism was dose dependent on the ASIV concentration (0.1–100 μg/ml). The change in the PAI-1 activity of the cells was parallel to the change in PAI-1 antigen (data not shown). FIG. 16 shows the effect of ASIV on the endotoxin induced expression of tissue factor (TF) in HUMECs. ASIV antagonizes completely the LPS induced TF upregulation.

A significant increase in the TF mRNA is observed after treatment of HUVECs with LPS. The LPS increased TF mRNA value was antagonized in a similar manner by coincubation with ASIV (FIG. 17).

EXAMPLE 10
Effects of extracts which contain notoginseng R1 on the fibrinolytic activity in humans.

In FIGS. 18, 19 and 20 the effects of NR1 containing extracts on tPA, PAI and uPA on healthy test subjects is given. There is an increase of tPA and a decrease in PAI-1 which correspond to the effects of NR1 or ASIV in tissue culture.

We claim:
1. A method of directly blocking liberation of a bacterial endotoxin in a mammalian subject by administering a therapeutically effective amount of a triterpensaponin to the subject in need of treatment.
2. The method of directly blocking liberation of a bacterial endotoxin defined in claim 1 wherein the triterpensaponin is notoginsenoside or astragaloside.
3. The method of directly blocking liberation of a bacterial endotoxin defined in claim 1 wherein the triterpensaponin is derived from Panax notoginseng.
4. A method for regulating synthesis of tissue plasminogen activator and plasminogen activator inhibitor-1 in endothelial cells of a mammalian subject in need of said treatment which comprises the step of administering a therapeutically effective amount of a triterpensaponin selected from the group consisting of a notoginsenoside or an astragaloside to the mammalian subject.
5. The method for regulating synthesis of tissue plasminogen activator and plasminogen activator inhibitor-1 defined in claim 4 wherein the triterpensaponin is Notoginsenoside R1 or Astragaloside IV.

* * * * *